(12) United States Patent
Atkins et al.

(10) Patent No.: US 11,857,718 B2
(45) Date of Patent: Jan. 2, 2024

(54) ON-DEMAND, PORTABLE CONVECTION VAPORIZER

(71) Applicant: JUUL Labs, Inc., San Francisco, CA (US)

(72) Inventors: Ariel Atkins, San Francisco, CA (US); Adam Bowen, San Mateo, CA (US); Steven Christensen, Burlingame, CA (US); Alexander J. Gould, Coeur d'Alene, ID (US); Nicholas J. Hatton, Oakland, CA (US); Esteban Leon Duque, Berkeley, CA (US); Kevin Lomeli, San Francisco, CA (US); James Monsees, San Francisco, CA (US); Matthew J. Taschner, Bend, OR (US)

(73) Assignee: JUUL Labs, Inc., Washington, DC (US)

( * ) Notice: Subject to any disclaimer, the term of this patent is extended or adjusted under 35 U.S.C. 154(b) by 128 days.

(21) Appl. No.: 17/139,317

(22) Filed: Dec. 31, 2020

(65) Prior Publication Data
US 2021/0369985 A1    Dec. 2, 2021

Related U.S. Application Data

(63) Continuation of application No. 16/693,020, filed on Nov. 22, 2019, now Pat. No. 10,905,167, which is a
(Continued)

(51) Int. Cl.
| | |
|---|---|
| *A24F 40/20* | (2020.01) |
| *A24F 40/40* | (2020.01) |
| *A61M 11/04* | (2006.01) |
| *A24F 40/46* | (2020.01) |

(Continued)

(52) U.S. Cl.
CPC .......... *A61M 11/042* (2014.02); *A24F 40/40* (2020.01); *A24F 40/46* (2020.01); *A24F 40/485* (2020.01); *A24F 40/53* (2020.01); *F22B 1/284* (2013.01); *H05B 3/44* (2013.01); *A24F 40/20* (2020.01); *A61M 15/0021* (2014.02); *A61M 2016/0024* (2013.01); *A61M 2016/0027* (2013.01); *A61M 2205/3317* (2013.01); *A61M 2205/3368* (2013.01); *A61M 2205/3592* (2013.01);
(Continued)

(58) Field of Classification Search
CPC ....... A61M 11/042; A24F 40/42; A24F 40/40; A24F 40/20; A24F 40/46; H05B 3/44
See application file for complete search history.

(56) References Cited

U.S. PATENT DOCUMENTS

| | | | |
|---|---|---|---|
| 9,591,876 B2 * | 3/2017 | Alima | ..................... A24F 40/46 |
| 10,517,331 B2 * | 12/2019 | Atkins | ................. A61M 11/042 |

(Continued)

*Primary Examiner* — Hae Moon Hyeon
(74) *Attorney, Agent, or Firm* — Mintz, Levin, Cohn, Ferris, Glovsky and Popeo, P.C.

(57) ABSTRACT

On-demand, hand-held vaporizer that operates primarily by convection. The vaporizer is configured to permit very rapid (e.g., within a few seconds) heating of air drawn through an oven chamber to a predetermined or selectable vaporizing temperature to vaporize a material (e.g., loose leaf plant material, etc.) that is held in the oven chamber. The vaporizer provides efficient transfer of air being heated as well as rapid delivery of vaporizable material to a user.

16 Claims, 18 Drawing Sheets

Related U.S. Application Data continuation of application No. 15/625,979, filed on Jun. 16, 2017, now Pat. No. 10,517,331.

(60) Provisional application No. 62/441,090, filed on Dec. 30, 2016, provisional application No. 62/351,272, filed on Jun. 16, 2016.

(51) Int. Cl.

| | | |
|---|---|---|
| *A24F 40/485* | (2020.01) | |
| *A24F 40/53* | (2020.01) | |
| *F22B 1/28* | (2006.01) | |
| *H05B 3/44* | (2006.01) | |
| *A61M 16/00* | (2006.01) | |
| *A61M 15/00* | (2006.01) | |

(52) U.S. Cl.
CPC ............... *A61M 2205/3606* (2013.01); *A61M 2205/3653* (2013.01); *A61M 2205/50* (2013.01); *A61M 2205/505* (2013.01); *A61M 2205/581* (2013.01); *A61M 2205/582* (2013.01); *A61M 2205/583* (2013.01); *A61M 2205/8206* (2013.01)

(56) References Cited

U.S. PATENT DOCUMENTS

| | | | | |
|---|---|---|---|---|
| 10,905,167 | B2* | 2/2021 | Atkins | A24F 40/46 |
| 11,019,846 | B2* | 6/2021 | Ding | A24F 40/42 |
| 11,253,001 | B2* | 2/2022 | Atkins | A24F 40/46 |
| 11,330,840 | B2* | 5/2022 | Fernando | A24F 1/30 |
| 2009/0293892 | A1* | 12/2009 | Williams | A24F 40/42 |
| | | | | 131/194 |
| 2012/0325227 | A1* | 12/2012 | Robinson | A61M 16/108 |
| | | | | 131/328 |
| 2017/0215478 | A1* | 8/2017 | Harrison | A24F 40/46 |
| 2017/0224018 | A1* | 8/2017 | Li | A24F 40/46 |
| 2018/0084823 | A1* | 3/2018 | Fuisz | A24B 15/243 |

* cited by examiner

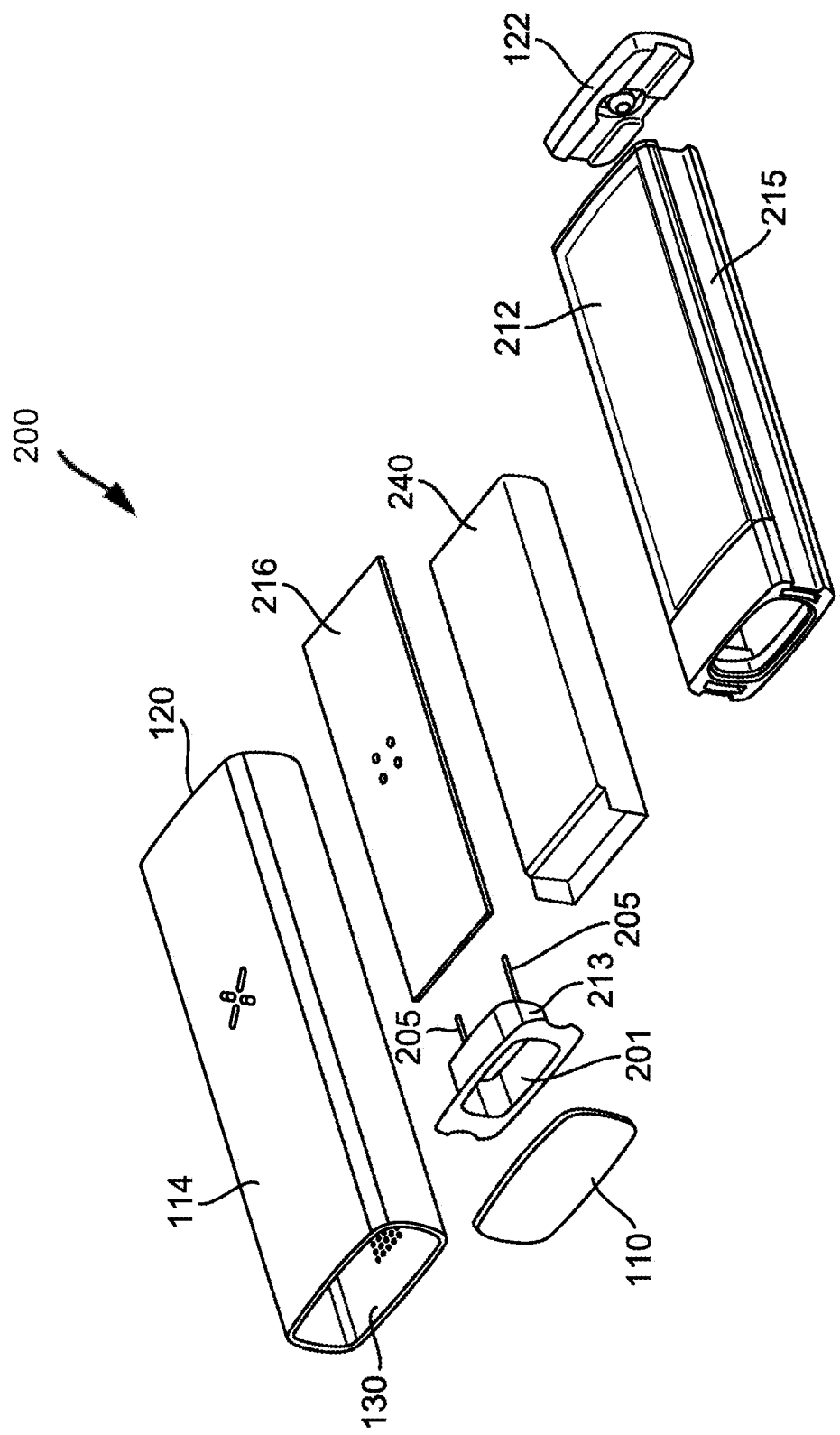

ON-DEMAND, PORTABLE CONVECTION VAPORIZER

CROSS REFERENCE TO RELATED APPLICATIONS

This application is a continuation of U.S. patent application Ser. No. 16/693,020, filed on Nov. 22, 2019, now issued as U.S. Pat. No. 10,905,167, and entitled "On-Demand, Portable Convection Vaporizer," which is a continuation of U.S. application Ser. No. 15/625,979, filed on Jun. 16, 2017, now issued as U.S. Pat. No. 10,517,331, and entitled "On-Demand, Portable Convection Vaporizer," which claims priority to U.S. Provisional Patent Application Nos. 62/351,272, filed on Jun. 16, 2016 and entitled "Electronic Vaporizer Devices," and 62/441,090, filed on Dec. 30, 2016 and entitled "On-Demand Portable Convection Vaporizers," the disclosures of each of which are incorporated herein by reference in their entirety.

BACKGROUND

Vaporizing devices, including electronic vaporizers or e-vaporizer devices, allow the delivery of vapor containing one or more active ingredients by inhalation of the vapor. Electronic vaporizer devices are gaining increasing popularity both for prescriptive medical use, in delivering medicaments, and for consumption of tobacco and other plant-based smokeable materials, such as cannabis, including solid (e.g., loose-leaf) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use. Typically, such devices are controlled by one or more switches, buttons, or the like (controls) on the vaporizer, although a number of devices that may wirelessly communicate with an external controller (e.g., smartphone) have recently become available.

Vaporization by the application of heat may be performed by convection, conduction, radiation and/or other means, including various combinations of these. Although vaporizers that apply heat primarily by convection (so-called convection-based vaporizers) have been described, they are typically slower to heat and therefore less convenient than other, e.g., conduction or primarily conduction, vaporizers. In particular, it has been challenging to provide a portable/hand-held convection-based vaporizer that is sufficiently "on-demand" to provide immediate or near-immediate (e.g., within a few seconds or less) vaporization of a vaporizable material when a user draws on the vaporizer. Currently available convection-based portable vaporizers on the market do not provide such on-demand heating and vaporization. Typically, convection-based portable vaporizers require some set amount of heat-up time in order for the device to properly vaporize the material of interest, that may be lengthy enough to be often inconvenient to users, and may also take further time to cool down For example, previously described convection-based portable vaporizers require some form of physical selection input from the user to turn on or enable the device. This has typically been executed through some form of mechanical switch or push-button; once the device is turned on, there is some amount of time (on the order of tens of seconds or minutes) required for the device to reach proper vaporization temperatures before the user can actively draw vapor using the device effectively. Using such convection-based portable vaporizers, some portion of any active ingredient of the vaporizable material can be lost to the ambient environment (and thereby unavailable to the user) due to, for example, relatively lengthy nonuse warm-up and cool-down periods at elevated temperatures and internal features of the vaporizers. In addition, such convection-based vaporizers may not be able to tightly control the air temperature that comes in contact with the material. That lack of air temperature control, together with varying air flow rates induced by the user, the quality and quantity of the produced vapor may vary significantly. In particular, many so-called on-demand or "instant heat-up" vaporizers suffer from this problem; although the heating element may heat up very quickly, the air flow may not be adequately and/or uniformly heated. This may be due, at least in part, to the large thermal mass surrounding the heater, and wasted energy dissipated into the device instead of the circulating air. This may result in the user having to take multiple "puffs" or wait for an extended period of time before the device can produce quality vapor in adequate quantities for user satisfaction.

SUMMARY

Aspects of the current subject matter relate to an on-demand, portable convection vaporizer device that provides efficient transfer of air being heated as well as rapid delivery of vaporizable material to a user.

A vaporizer consistent with certain implementations of the current subject matter includes a vaporizer body with an outer housing; a heater within the vaporizer body, the heater having at least one opening through which air is passed and heated; an oven chamber in which a vaporizable material is held configured to be heated by the air heated by the heater, causing the vaporizable material to at least partially vaporize into the heated air; a controller coupled to the heater and configured to cause the heater to heat to a temperature; and a mouthpiece configured to deliver the heated air and vaporized material.

A vaporizer consistent with certain implementations of the current subject matter includes a vaporizer body having an outer housing and an inner structural housing contained within the outer housing and defining a cavity; an air inlet extending through a portion of the outer housing and into the cavity of the inner structural housing, through which air enters into the cavity; a heater suspended within the cavity of the inner structural housing, the heater having one or more openings through which the air is passed, the heater and the plurality of openings generating turbulence in the air as the air is passed over and through the heater for heating; an oven chamber within the cavity of the inner structural housing and in which a vaporizable material is held configured to be heated by the air heated by the heater, causing the vaporizable material to vaporize into the heated air; a controller coupled to the heater and configured to cause the heater to heat to a predetermined temperature upon air flow to the heater being detected; and a mouthpiece configured to deliver the heated air and vaporized material.

A method consistent with certain implementations of the current subject matter includes sensing a draw on a mouthpiece of a vaporizer; applying energy to a heater of the vaporizer; monitoring an air temperature of heated air from the heater; limiting an oven temperature of an oven chamber of the vaporizer by modifying the energy applied to the heater; and regulating a heater temperature of the heater to control the heater temperature in response to changes in resistance of the heater.

A vaporizer consistent with certain implementations of the current subject matter includes a vaporizer body comprising an outer housing; a heater within the vaporizer body, the heater configured to disturb the flow of and heat air flowing in the region of the heater; an oven chamber fluidly coupled to the heater in which a vaporizable material is held, configured to be heated by the air heated by the heater, causing the vaporizable material to vaporize into the heated air; and a mouthpiece configured to deliver the heated air and vaporized material.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to vaporizer devices, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 2 illustrates, via an exploded view, features of the exemplary vaporizer device consistent with implementations of the current subject matter;

When practical, similar reference numbers denote similar structures, features, or elements.

DETAILED DESCRIPTION

Figure 1A:
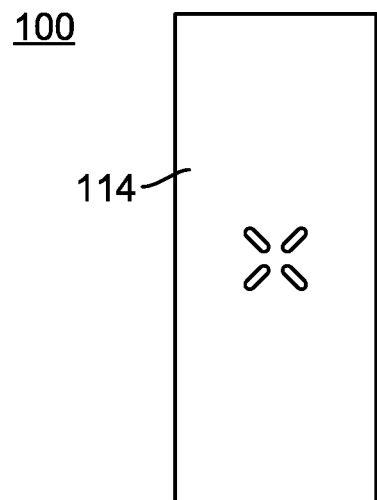
FIGS. 1A-1D illustrate exterior features of an exemplary vaporizer device consistent with implementations of the current subject matter.

Implementations of the current subject matter include methods and devices relating to vaporizing of one or more materials for inhalation by a user. The term "vaporizer" is used generically in the following description and refers to a vaporizer device. Examples of vaporizers consistent with implementations of the current subject matter include electronic vaporizers, electronic cigarettes, e-cigarettes, or the like. In general, such vaporizers are often portable, frequently hand-held devices that heat a vaporizable material to provide an inhalable dose of the material.

A vaporizer consistent with certain implementations of the current subject matter is a hand-held device that operates primarily by convection to provide efficient transfer of air being heated as well as rapid delivery of vaporizable material to a user.

Vaporizers consistent with certain implementations of the current subject matter are configured to permit very rapid (e.g., within 3 seconds, within 2 seconds, within 1 second, etc.) heating of air drawn through an oven chamber to cause vaporizable material (e.g., loose leaf plant material, etc.) in the oven chamber to be heated to a target vaporization temperature. The oven chamber may be thermally conductive (to permit additional heating and vaporization of the material within the oven) or thermally insulating (to resist transfer of heat to the oven, so that heat is transferred just to the vaporizable material). The oven chamber may be present at the distal end of the device, opposite from a proximal mouthpiece. Alternatively, the oven chamber may be located adjacent or in close proximity to the mouthpiece, for example below or adjacent a mouthpiece portion of the device.

The oven chamber may be connected near the distal end of the device (e.g., to a frame or skeleton of the vaporizer) though one or more contacts; however, some or a majority of the oven chamber may be surrounded by an air gap (or other thermal isolation means, for example insulating material) to reduce transfer of heat from the oven chamber to the rest of the apparatus. The oven chamber may include a lid. The oven chamber may be manufactured as a deep drawn oven, e.g., may have a depth, width, and breadth, wherein the depth (the distance from the inside of the lid to the bottom, e.g., screen) of the oven chamber, for example, may be between 0.3× and 2× the width of the oven; the breadth may be between 0.1× and 1× the width. Generally, the oven chamber may be sized for an intended use of the vaporizer device in which it is housed, and/or the oven chamber may be sized based on manufacturing considerations. The oven chamber may have solid walls, perforated walls, a basket-weave structure, or some other configurations of solid and open areas, or combinations of these, configured to reasonably contain the material to be vaporized. The oven chamber can be configured to accept a further inner vessel (not shown) which can contain vaporizable liquids or waxes or the like.

The heater (e.g., resistive heating element) may be positioned in the air path and configured for rapidly heating air passing around and/or through the heater. The heater may include one or more openings, passages, channels, slots, slits, etc., for passage of air through and/or around the heater, one or more of which such air passages may have irregular, jagged, fractal, protruding edges or the like which, together and/or separately with the configuration of the heater may create increased turbulent airflow through or around the heater, increasing the transfer of heat to the air as it passes through/around the heater. In one embodiment, the heater may be an elongate tube extending in a long axis, the tube having one or more cut-out regions along its length therethrough to generate turbulence in air passing transversely across and/or along the long axis of tube. In some variations, the heater can include one or more thin layers or sheets of material having a plurality of slots, slits, or cut-out regions through which air passes; these sheets may be folded, crumpled, layered, or the like; alternatively, in some variations the sheet is flat. In other variations, the heater can be a coil or string of resistive material, which can have surface variations, bumps, vanes, or the like to increase surface area, and thereby improve heat transfer to the air flowing around and through the heater.

In certain implementations of the current subject matter, the heater may be controlled by heater control circuitry that includes four-point inputs; a first pair of inputs may correspond to the heater power leads/inputs; the second pair of inputs/leads may be offset from the heater power inputs (and in some variations positioned between the heater power leads) and may be configured to sense the voltage drop across a region of the heating element. The four-point measurement control may be used to determine the temperature of the resistive heater with a relatively fine resolution (e.g., within +/−5° C., within +/−4° C., within +/−3° C., within +/−2° C., etc.). Alternatively, a two-point temperature sensing system can be used, where the same leads used for applying the heater power current also can apply a smaller current to measure a voltage drop across the leads, thereby measuring the heater temperatures at times different from when heater current is applied.

In addition, a temperature sensor (e.g., thermocouple, infrared sensor, or similar) may be deployed within the air flow path downstream of the heater (e.g., between the heater and the oven chamber, within the oven chamber, etc.) to sense the temperature of air flowing into, through, or around the oven chamber and vaporizing the material within the oven chamber. In any of the variations described herein, the temperature control circuitry may receive input from the heater (e.g., the resistance and therefore temperature of the heater via two- or four-point measurement) and may also receive input from the downstream air flow temperature sensor(s) (e.g., one or more thermistors in the entry for heated airflow into the oven chamber). The temperature control circuitry may be configured to, upon sensing negative pressure due to a user drawing on the mouthpiece, immediately deliver an elevated power (current) to the heater at a first frequency/duty cycle. This elevated power may near-immediately increase the temperature of the heater (e.g., >500° C.), but may be limited by the control circuitry to remain below a safety limit (e.g., 700° C.) or within a useful temperature range. The control circuitry may further monitor the temperature of the heated air that has passed over the heater prior to entering the oven chamber (e.g., via the one or more thermistors) and may limit the temperature of the oven chamber (e.g., by modifying the power applied and/or the frequency/duty cycle of the power applied to the heater) as part of a control loop. Thus, the vaporization temperature, corresponding to the temperature of the air applied to vaporize the material within the oven chamber, may be kept at a desired target temperature, or within a desired or useful temperature range.

The target temperature may be predetermined (e.g., preset on the device) and/or may be user selected or user modified. The target temperature may be a single temperature or a plurality of temperatures, including a temperature profile (e.g., a plurality of temperatures over time), or an acceptable temperature range. The user may input absolute temperatures (e.g., degrees Celsius or Fahrenheit) or may modulate predetermined temperatures (up or down).

In general, the vaporizer devices consistent with some implementations of the current subject matter may be configured for use with a loose-leaf, or liquid or wax or other vaporizable material. Any of these devices may be configured to wirelessly connect to one or more devices, including user-controlled devices, to modify operation of the vaporizer device. For example, the devices described herein may wirelessly communicate with a user interface that allows dosing control (dose monitoring, dose setting, dose limiting, user tracking, etc.), locational information (e.g., location of other users, retailer/commercial venue locations, vaping locations, etc.), vaporizer personalization (e.g., naming the vaporizer, locking/password protecting the vaporizer, parental controls, associating the vaporizer with a user group, registering the vaporizer, etc.), and engaging in social activities (games, groups, etc.) with other users.

A vaporizer device consistent with implementations of the current subject matter may include a stack-up arrangement of circuit board and battery and other components. The oven chamber may be comparatively large compared to the overall size of the vaporizer device, yet have a relatively small thermal mass, allowing it to heat rapidly (e.g., within 1 second or less) to the vaporization temperature of the material (e.g. for tobacco, between 100° C. and 300° C.). Thus the relative size/ratio of vaporization chamber can be greater when compared to other devices. Overall the device may be thin and small. Since the device may heat quickly (within 1 second or less) to vapor, and energy losses due to thermal mass around the convective heating path can be kept relatively low, a user applying a puff (or if the device is lip sense activated) (or, alternatively, a user turning on (e.g., selecting or depressing a button or the like)) may need only a three to four second puff to get a satisfying amount of vapor almost instantly, effectively duplicating the effect of conventional combustion-based cigarettes, cigars, pipes or the like, increasing user satisfaction.

Consistent with some implementations of the current subject matter, a vaporizer may have a large, or even unlimited number of customizable temperature settings. A number of sessions per charge and a number of user puffs per charge, as well as a charge time of the vaporizer device, may be based on the size of battery that is used.

Figure 1B:
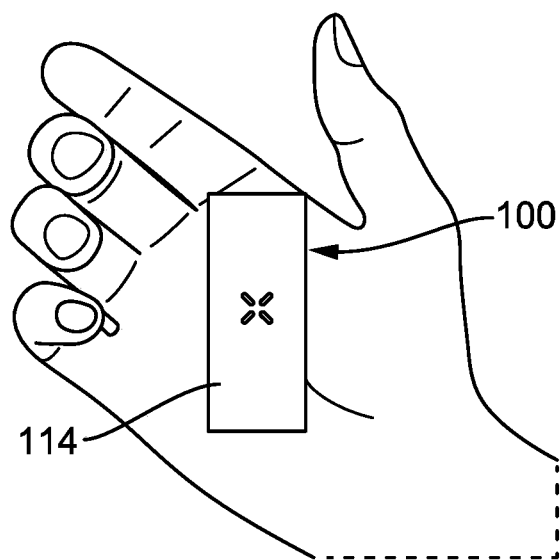
Figure 1C:
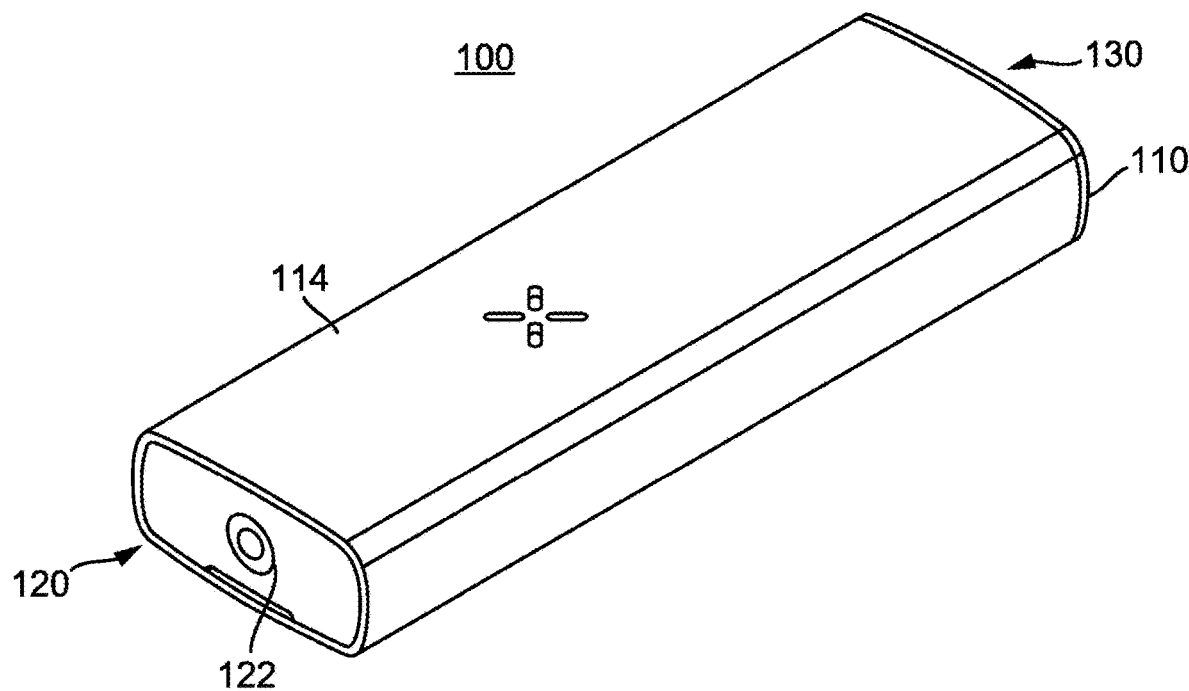
Figure 1D:
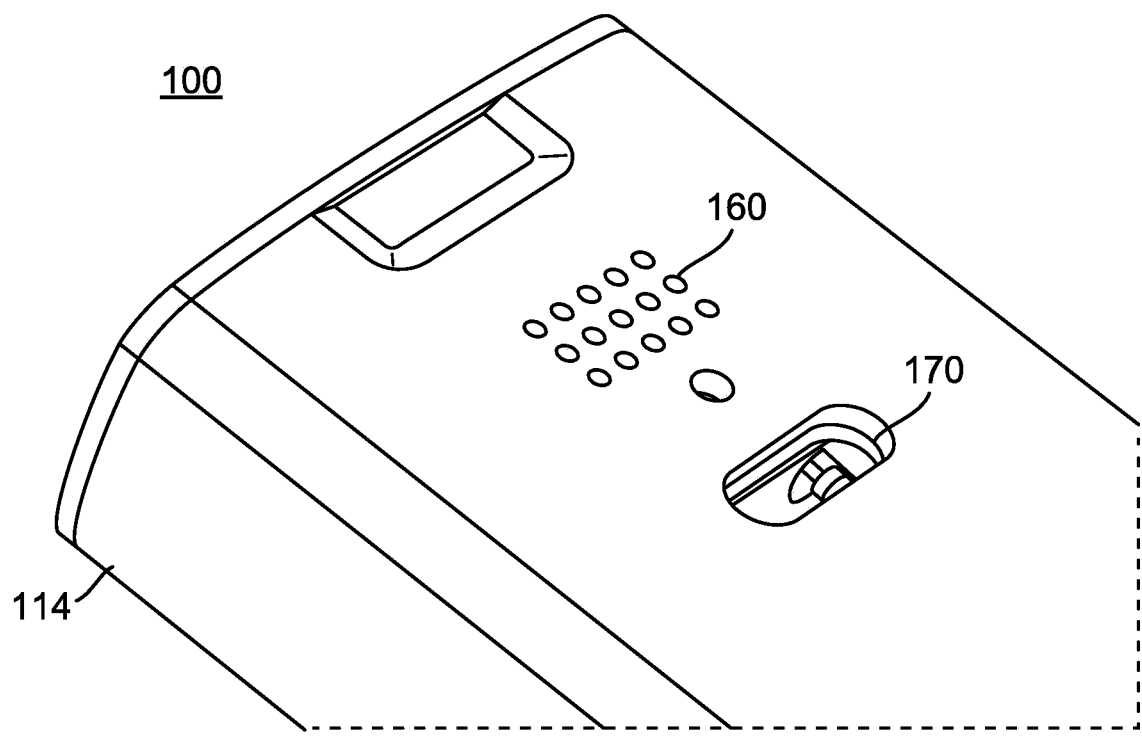

With reference to FIGS. 1A-1D, exterior features of an exemplary vaporizer device 100 consistent with implementations of the current subject matter are illustrated. As shown, the vaporizer device 100 may have an elongate or generally rectangular shape with two opposing end portions shorter in length than two opposing side portions. However, variations of the size and shape of a vaporizer consistent with implementations of the current subject matter are possible. For example, the vaporizer device 100 may have an essentially square, tubular, spherical, faceted, ovoid, or other shape, or combinations thereof. A vaporizer consistent with implementations of the current subject matter may be compact and sized to easily fit within a hand of a user, as shown in FIG. 1B. The vaporizer device 100 has an outer housing 114, a mouthpiece 122 at a top (or proximal) end 120, and a lid 110 at a bottom (or distal) end 130. As shown in FIG. 1D, inlet air holes 160 are provided on and extend through the outer housing 114. A universal serial bus (USB) charging port 170 is also provided extending through the outer housing 114.

FIG. 2, via an exploded view, illustrates several of the features of the vaporizer device 100. Internal to the outer housing 114 is a structural housing component 212. One or more side air channels 215 (one shown in FIG. 2) may be formed into one or more respective side surfaces of the structural housing component 212. Consistent with some implementations of the current subject matter, the structural housing component 212 may be made from a ceramic material, other insulating material, or other material (such as metal) thermally insulated from the heater. A battery 240 and a printed circuit board (PCB) 216 are layered and contained within the structural housing component 212. A portion of an oven chamber 201 with a housing 213 is also contained within the structural housing component 212 near end 130 of the vaporizer 200. Electrical leads 205 are shown extending from within the housing 213. The lid 110 covers an open portion of the oven chamber 201. The mouthpiece 122 is at the end 120 of the vaporizer 200.

Figure 3:
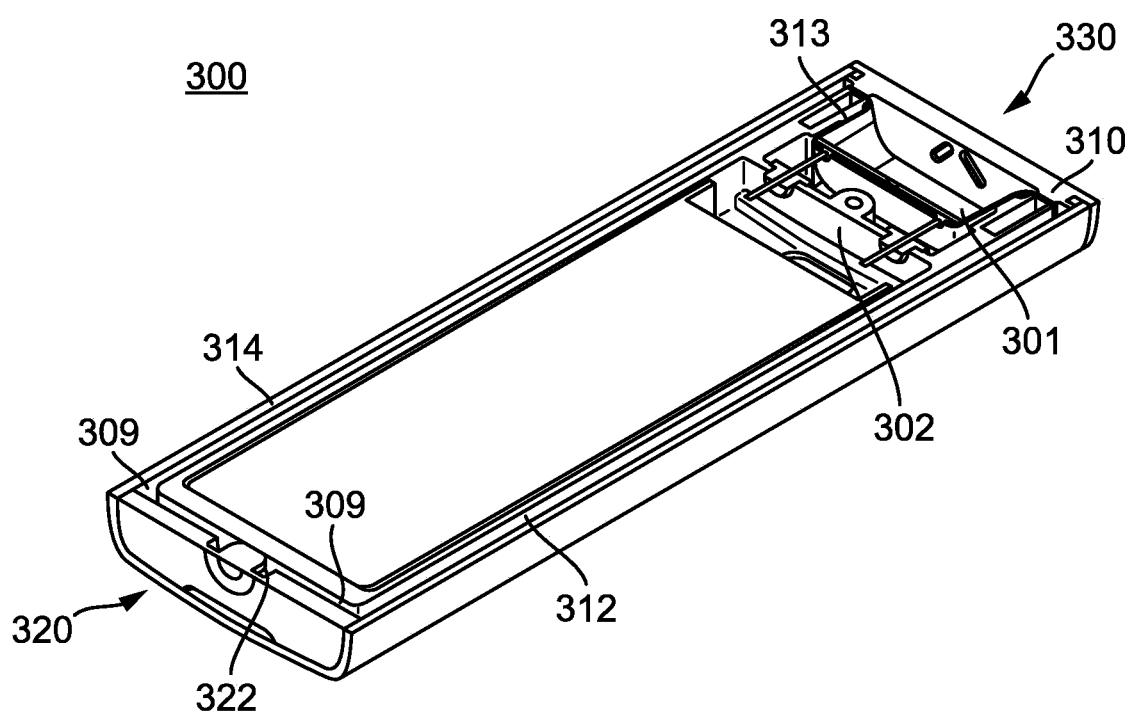
FIG. 3 illustrates, via a cross-sectional view, features of an exemplary vaporizer device consistent with implementations of the current subject matter.

FIG. 3, via a cross-sectional view, illustrates several features of a vaporizer device 300. As shown in FIG. 3, the vaporizer device 300 includes, near (e.g., nearly adjacent or adjacent) the bottom end 330, an internal oven chamber 301 with a surrounding oven housing 313. The lid 310 mates or otherwise attaches to the outer housing 314 at the bottom end 330. The mouthpiece 322 mates or otherwise attaches to the outer housing 314 at the top end 320. Internal to the outer housing 314 is a structural housing component 312. One or more internal side slots or channels 309 are formed between and extend along the lengths of outer side walls of the structural housing component 312 and inner side walls of the outer housing 314. The internal side channel 309 extends from the oven chamber 301 to the mouthpiece 322, providing a cooling pathway for the vaporizable material to be inhaled by a user.

Heater 302 is a flat-plated heater which may allow for fast heat-up and is capable of high watt density (e.g., ~60 W/in2) and may have a high (~700° C.) operating temp limit, driven by melting point of the dielectric.

Figure 4A:
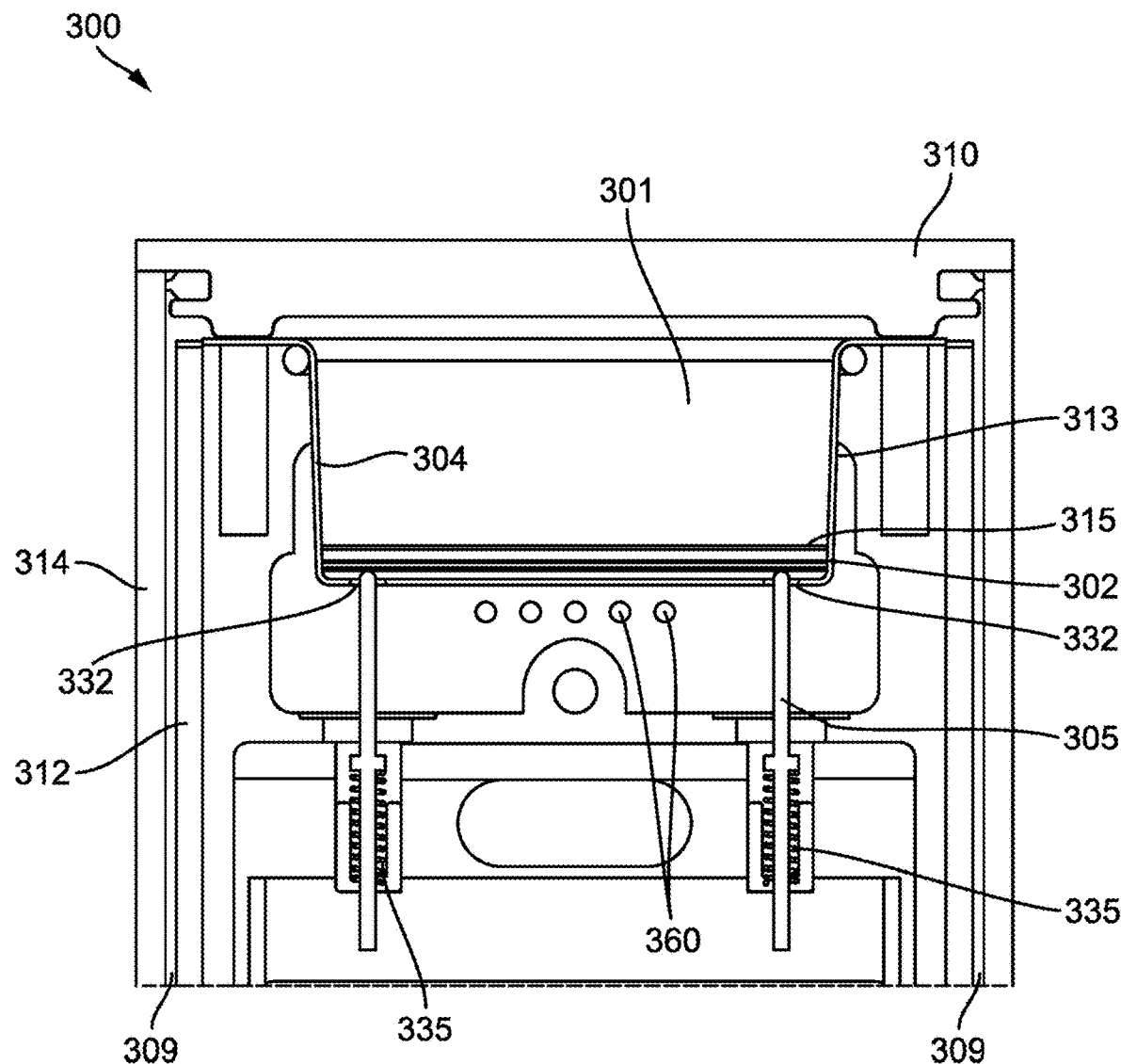
FIGS. 4A-4E illustrate various features of the exemplary vaporizer device of FIG. 3.
Figure 4B:
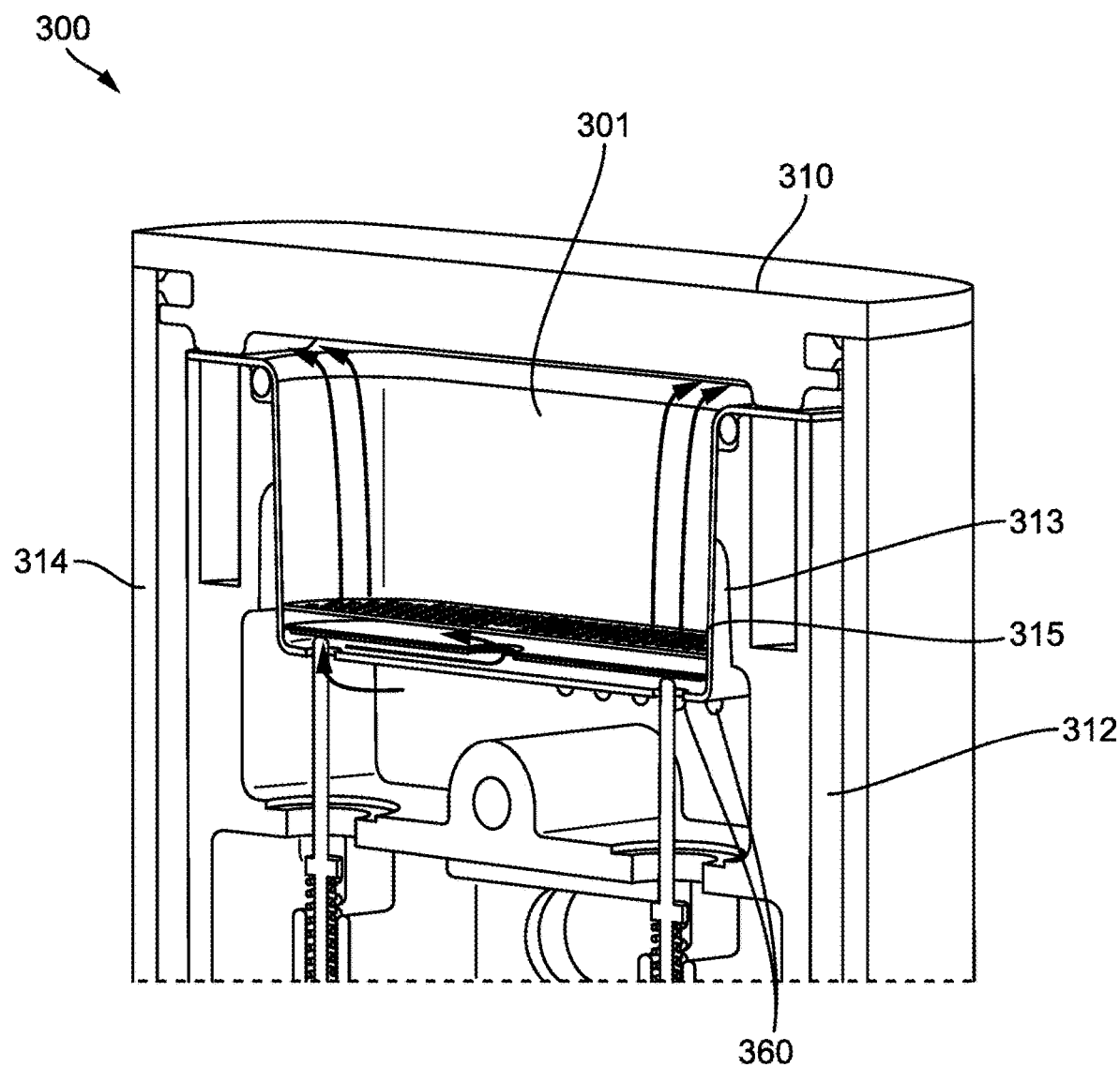
Figure 4C:
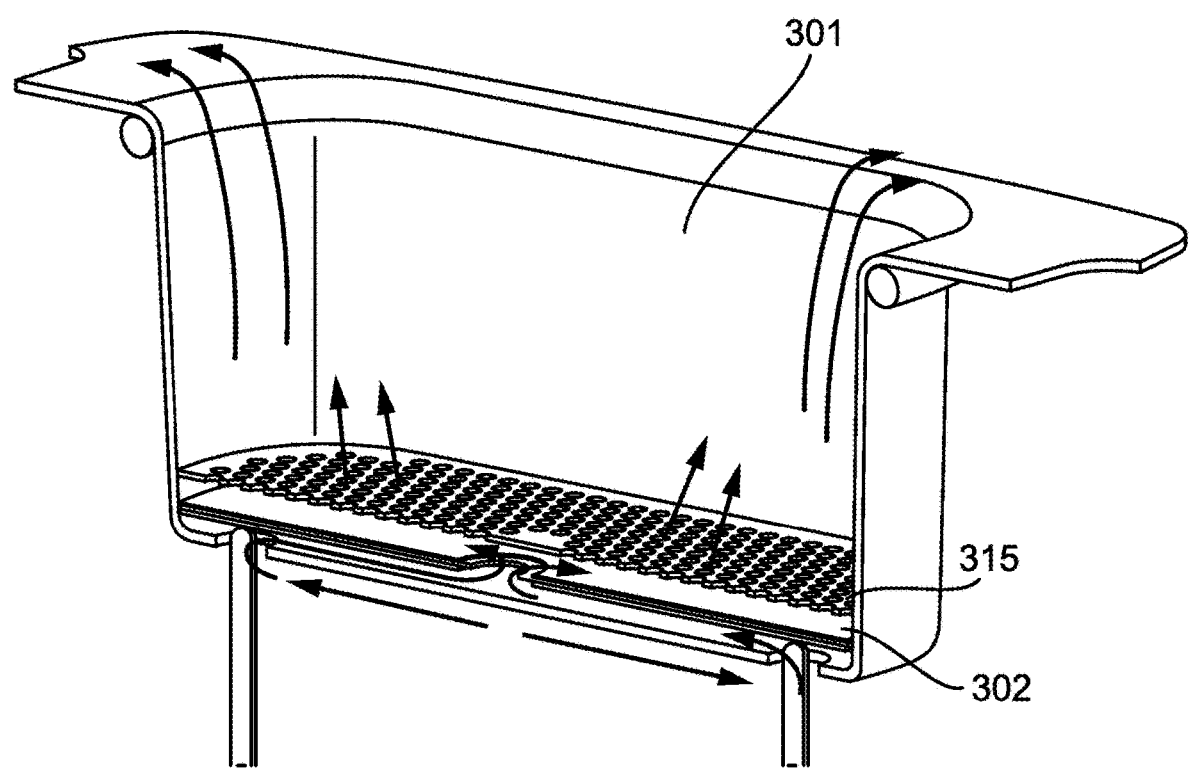

FIGS. 4A-4E illustrate various features of the exemplary vaporizer device of FIG. 3. FIG. 4A illustrates, via a cross-sectional view, features of an oven chamber 301 and heater 302, and FIGS. 4B and 4C illustrate airflow therethrough consistent with some implementations of the current subject matter. As shown, heated air flows up from heater 302 through the oven chamber 301 containing the vaporizable material, and back around over the edge of the oven chamber 301. Lead 305 is shown connected to the heater 302.

In some implementations of the current subject matter, as shown in FIG. 4A, a thermal conduction path is through a flange of the oven chamber 301, which may have a multiply perforated bottom (e.g., screen 315). The openings though the bottom may be arranged in a pattern to distribute the heated air evenly, e.g., having a hole density pattern that is greater on the outer region than the inner region, or other variations for equal or near equal heat distribution. An inlet air path may circulate around the outside of the oven 301, to reclaim any heat from the oven 301. The heater 302 may be mechanically captured between two bottoms of deep drawn parts (e.g., deep drawn oven, with another deep drawn part welded to it). The heater 302 may be welded and/or brazed to the oven chamber 301, or possibly mechanically captured. In some implementations of the current subject matter, the heater 302 may include a "thick film heater" that is anchored only at coolest points.

FIGS. 4A-4E also illustrate some additional features of the oven chamber 301 and surrounding areas of the vaporizer device 300, such as the outer housing 314, the structural housing component 312, and the lid 310. Also shown are two leads 305 and inlet air holes 360.

With reference to FIGS. 4B and 4C, the screen 315 may be installed within the oven chamber 301 to prevent the vaporizable material from contacting the heater 302. The heater 302 may be located ~1 mm (e.g., between 0.5 mm and 5 mm, between 0.5 mm and 3 mm, etc.) below the screen 315. The screen 315 and heater 302 may be constrained by perimeter welds or other means. FIGS. 4B and 4C illustrate air paths from air inlet into heater, circulating below, then through, then over the heater, and up into the oven chamber.

Figure 4D:
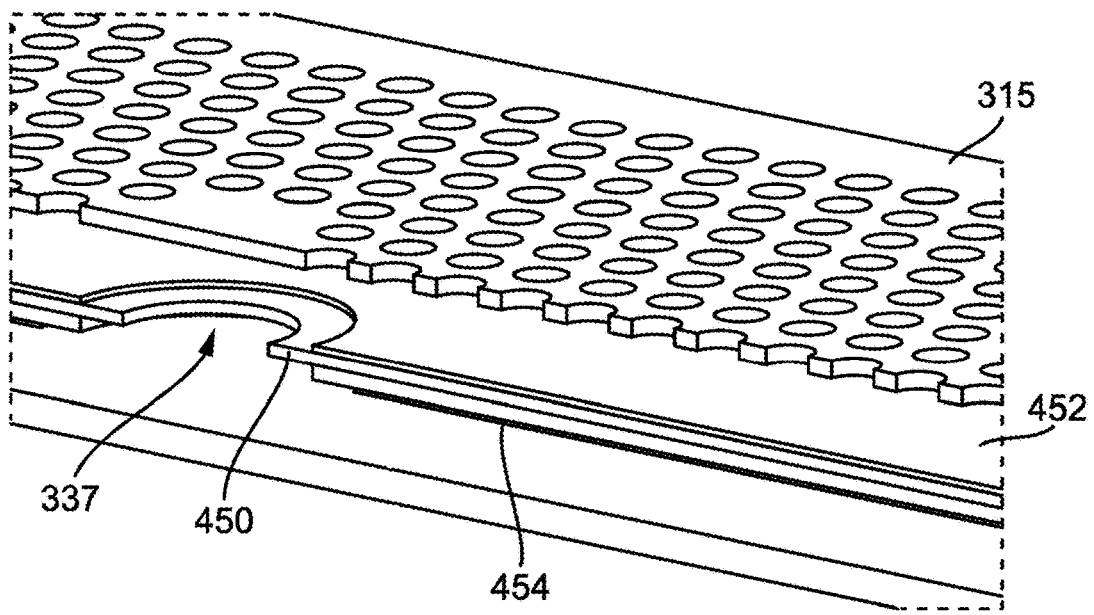
Figure 4E:
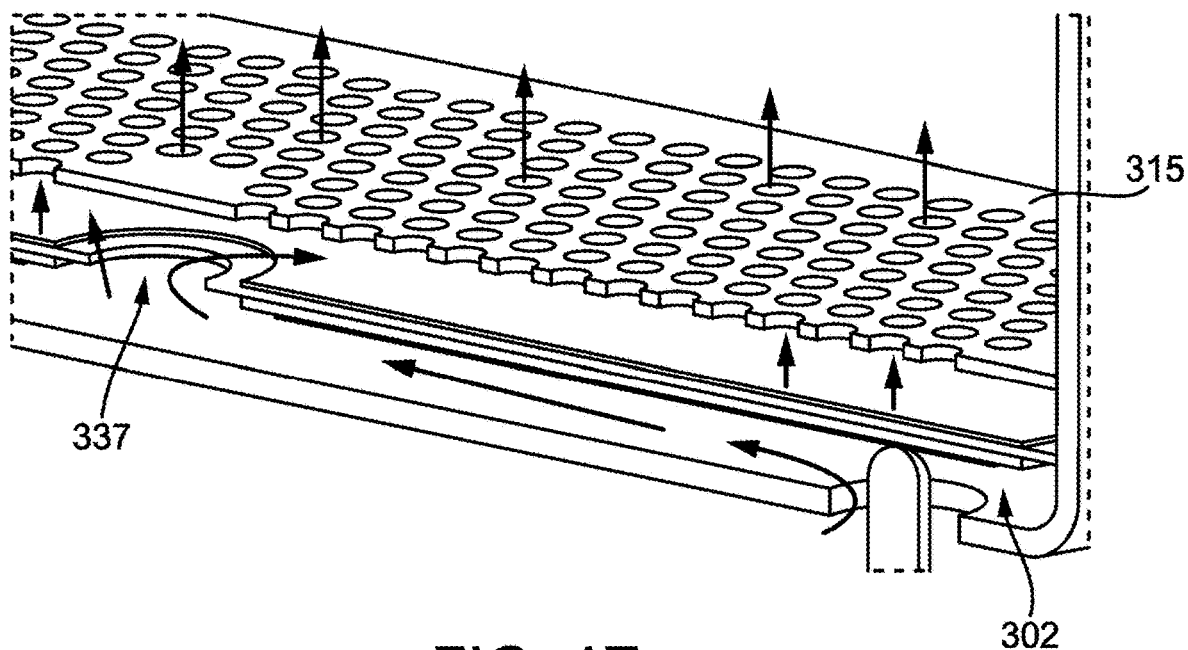

The heater 302 may be a low-mass composite structure. FIG. 4D shows an enlarged view of an example heater structure, and FIG. 4E shows airflow paths. Substrate 450 of the heater 302 may be, e.g., 0.003" 430 stainless steel. Each side of the heater substrate 450 may be coated with a thin layer, 0.002-0.003", of glass dielectric 452. The bottom layer of the heater 302 is the resistive heating element 454 which may be composed of a silver palladium alloy 0.001" thick. A thin layer of glass dielectric (not shown) may also be applied over the resistive element to mitigate oxidative damage. These glass and resistive layers may be applied as, for example, pastes using a screen-printing process.

In an embodiment, the heater 302 may include a stainless steel (SS) substrate with a glass dielectric layer, and a screen-printed resistive trace of ~0.010" total thickness.

In operation of the vaporizer 300 illustrated in FIGS. 3-4E, a user may remove the lid 310, load the oven chamber 302 with material to be vaporized, place the lid 310 back on, and take a puff from the device 300 on the opposite side of the device from the oven, where a mouthpiece is located. As the user draws on the mouthpiece, ambient air enters the device through the inlets of the outer housing 314, passes through the structural support housing 312 (e.g., skeleton) providing structural support for the oven chamber 301 and other internal components, enters the oven chamber 301 around cutouts 332 for leads 305, creating a pressure drop within the device which can be measured by a pressure sensor (not shown). When this pressure drop is detected, the heater 302 is powered by passing an electric current through it via the leads 305, causing the resistive element of the heater 302 to rapidly increase in temperature. The air being drawn into the oven chamber 301 will be heated as it passes under the heater 302, through a central hole 337 in the heater 302, and as it is deflected over the top of the heater by the non-porous region of the screen 315. The rest of the screen 315 is perforated to allow the hot air to readily pass through the material in the oven chamber 301 before it exits the top of the oven chamber 301 and runs down the side channels 309 in the frame (skeleton) to the user. The increased air turbulence generated by the structure of the device, including the airflows across the lower portion of the heater 302, through its central hole (or any number of other holes), then over its upper surface and then through oven screen 315 into the oven chamber 301 allows for efficient heat transfer from heater 302 to air to vaporizable material, increasing efficiency and time to vaporization.

To minimize energy loss from the heater 302, the oven may be very low mass (<0.25 mm walls), and may be thermally isolated. As shown in FIG. 4A, there may be a small air gap 304 between the oven chamber 301 and the structural housing 312 that acts as thermal insulation, aiding in the prevention of thermal sink (transfer) into the outer housing 314 from the heater 302. This way, much of the energy from the heater 302 in the form of heat will pass through the material to be vaporized rather than the body of the device 300, or it will transfer to the oven chamber 301 itself, which will also aid in vaporization (by conductive heating).

In the example of FIGS. 3-4E, a thermocouple is not shown, however one or more may be suspended within or over the central hole 337 in the heater 302, or somewhere within oven chamber 301. This may provide closed loop control of the air temperature. Although not necessary, a thermocouple would allow for faster vapor production since the heater 302 could be run at a higher temperature initially, and then be ramped down once the thermocouple indicates the desired vaporization air temperature.

Vaporizers consistent with implementations of the current subject matter may include a resistive heating element (e.g., heater 302) that is powered with an electric current through two terminals (e.g., leads 305). A precision resistance measurement circuit may be used to track resistance of the heating element when not heating and when heating to control the temperature of the heater 302 based on changes in heater material resistance.

In some implementations of the current subject matter, the vaporizer device has an "on"/active mode, but ideally the heater is fired only by triggering a pressure/flow sensor, by capacitive lip sensing, or by the user pressing a button for use, or the like.

Figure 5A:
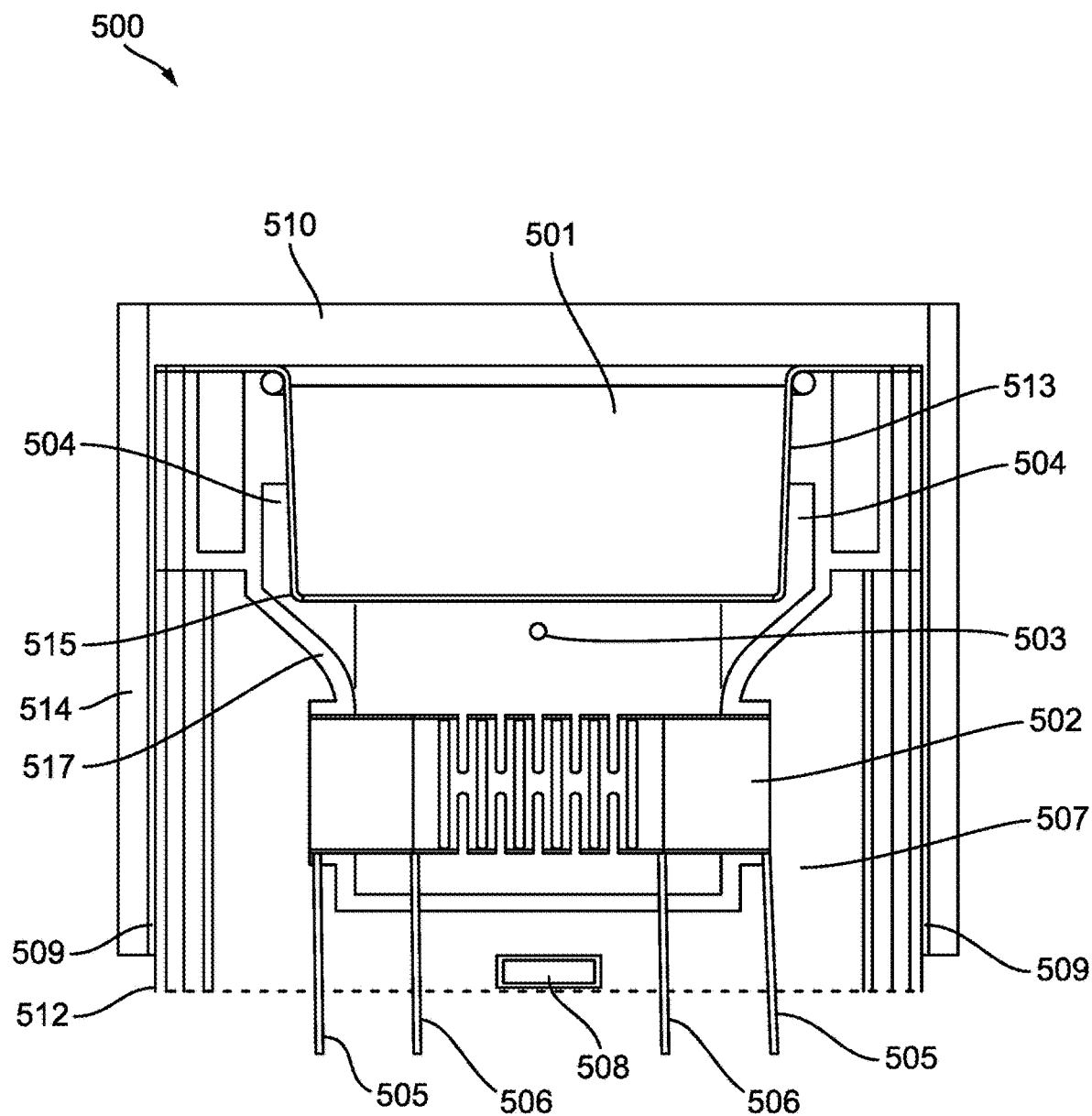
FIGS. 5A-5E illustrate various features of an additional exemplary vaporizer device consistent with implementations of the current subject matter.
Figure 5B:
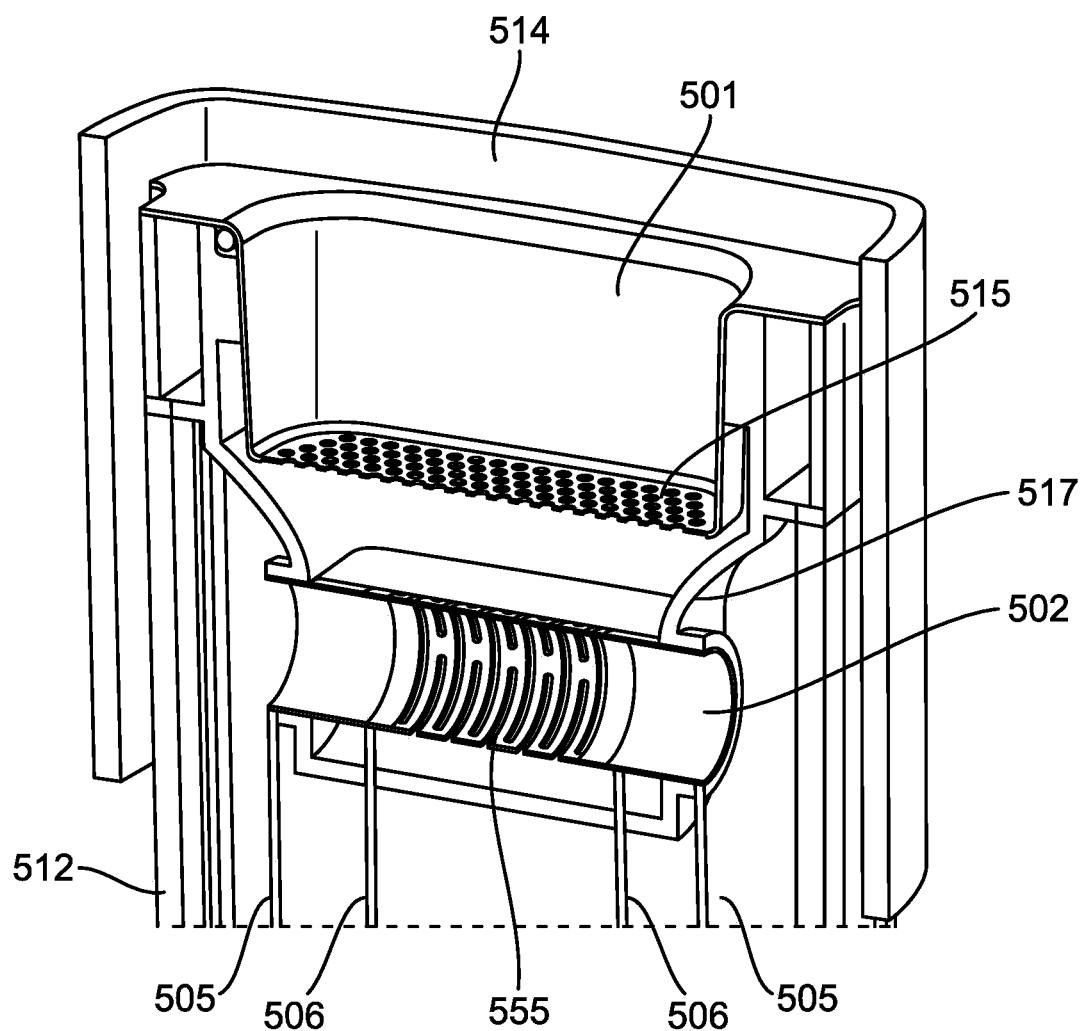
Figure 5C:
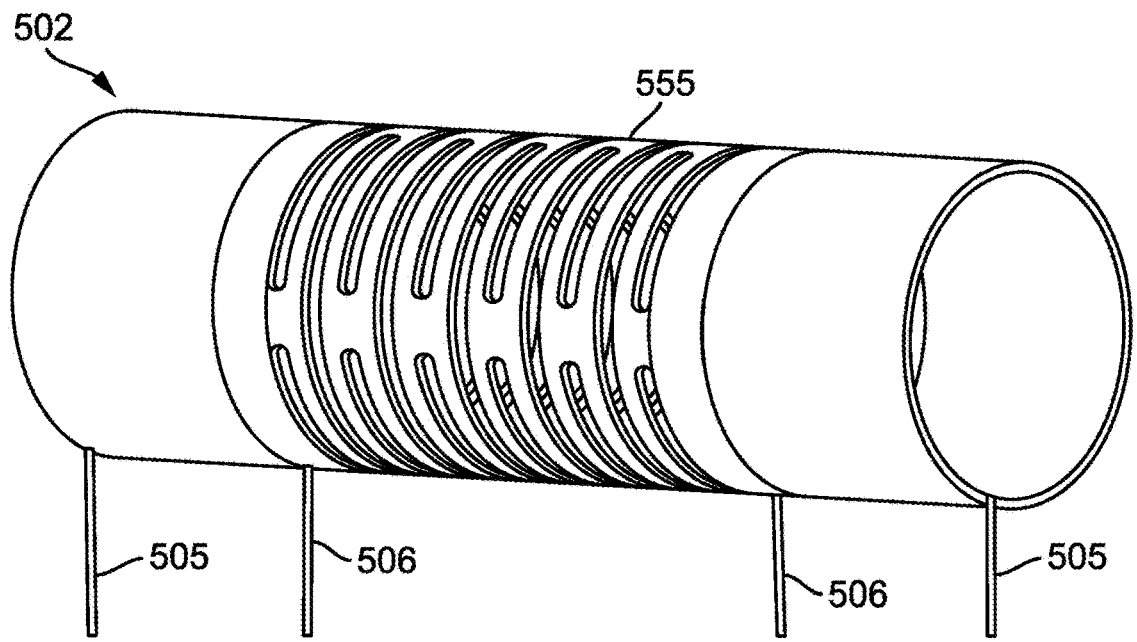
Figure 5D:
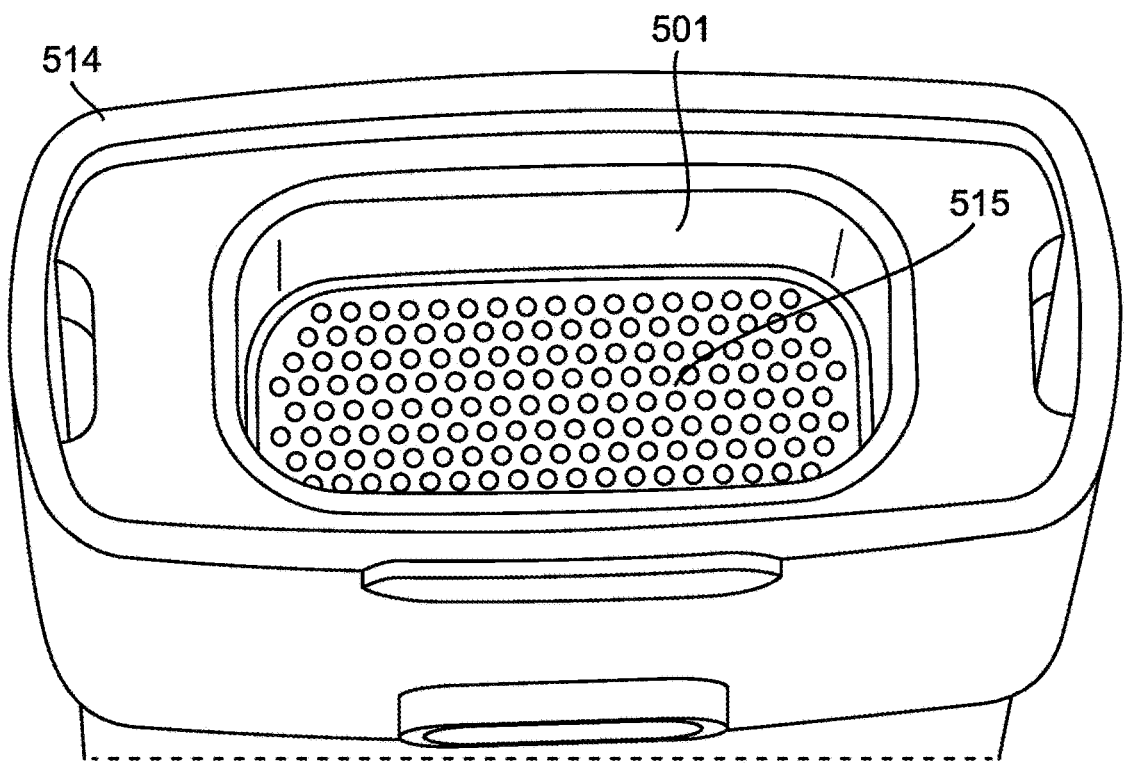
Figure 5E:
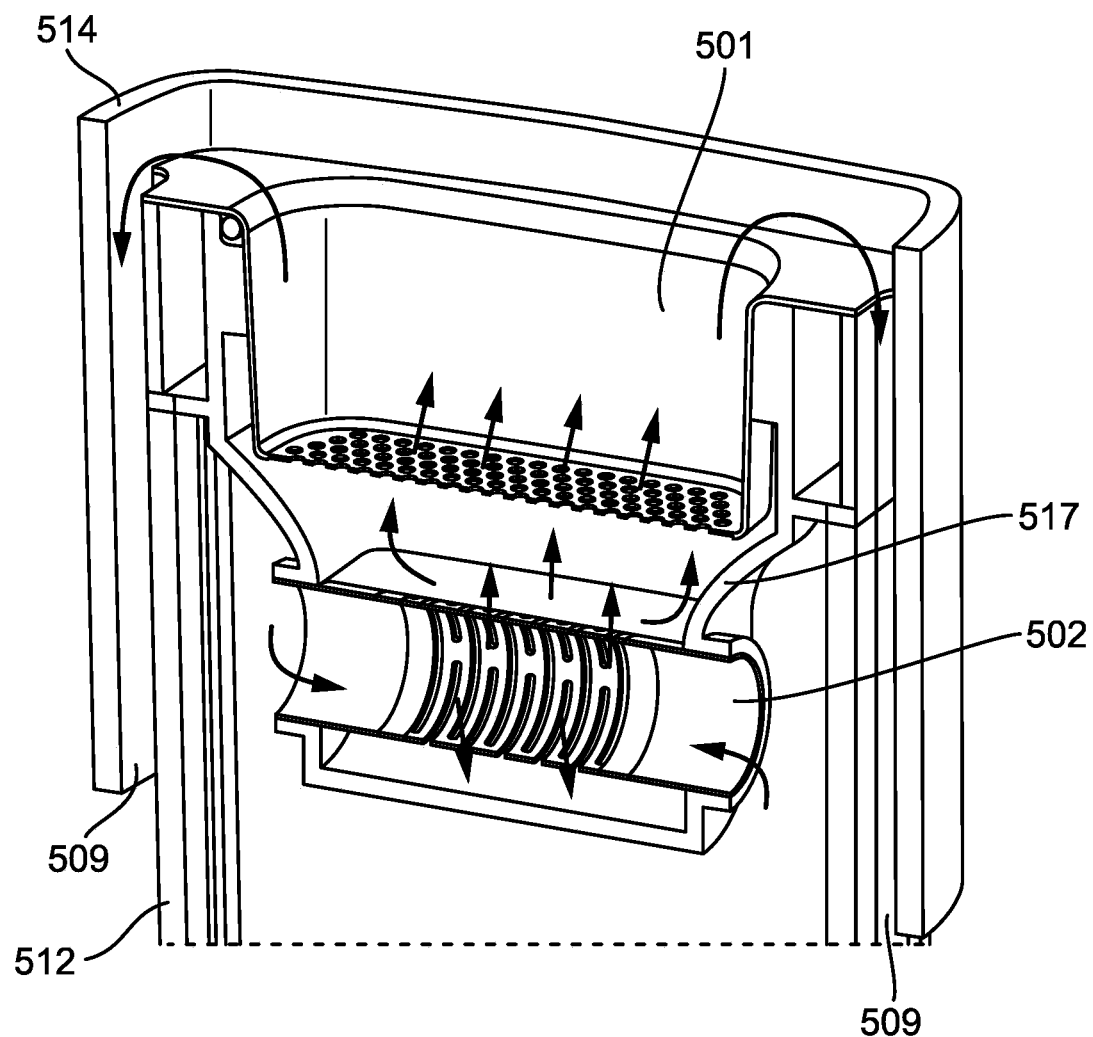

FIGS. 5A-5E illustrate, via various views, features of another exemplary vaporizer device 500 consistent with some implementations of the current subject matter. FIGS. 5A and 5B show a section through a front view of the vaporizer device 500, showing the heater assembly and oven assembly which can replace the heater and oven assembly shown in the overall vaporizer embodiment shown in FIGS. 1 through 4. The vaporizer device 500, consistent with implementations of the current subject matter, is configured as an on-demand, convection-based vaporizer. FIG. 5C illustrates an exemplary heater 502. FIG. 5D illustrates a top perspective view of the vaporizer device 500, showing details of an oven chamber 501. FIG. 5E illustrates airflow through the vaporizer device 500.

The vaporizer device 500 includes the oven chamber 501 that may hold a vaporizable material; this material may be packed or otherwise inserted into the oven chamber 501. The oven chamber (or oven) 501 may be formed by a progressive forming process. The vaporizable material (including loose-leaf vaporizable material) may be stored in the oven chamber 501 for vaporization. The vaporizer device 500 may also include an oven lid 510 that may cover, enclose, and/or seal a loading side of the oven chamber 501. The lid 510 may be attached over an accessible portion of the oven chamber 501 by various mechanisms, including a friction fit, a magnetic attachment, a mechanical attachment, some combination thereof, or the like. The vaporizer device 500 also includes a notched-tube heater 502 (e.g., heating assembly, convective heating assembly), which includes a heating element that may be placed directly or nearly adjacent (e.g., below in FIGS. 5A and 5B) the oven chamber 501 and may reside in an open chamber or cavity 507 within the elongate, flat body of the device 500. The notched-tube heater 502 may be a tube made from a type of resistive metal alloy that is notched or slotted via a process such as laser etching. A notched 555 region may provide a higher electrical resistance than the rest of the tube so that air (e.g., drawn by the user) passes through the slots with relatively more turbulence before coming in contact with the vaporizable material. The notched-tube heater 502 may be held in the air path, and coupled to the inner chamber of the vaporizer device 500 by a small number of contact points, or thermally or electrically insulating couplings, insulating lining, or the like, to minimize thermal transfer.

In operation, the vaporizer device 500 may be loaded with a vaporizable material by removing the oven lid 510 to load the oven chamber 501 with a desired vaporizable material. The user may then place the oven lid back on, and take a puff from the device 500 on the opposite side of the oven where a mouthpiece is located (e.g., mouthpiece 122 shown in FIG. 2). As the user draws on the mouthpiece, ambient air enters the device 500 (through the same sort of air inlets 160 of FIG. 1 and 360 of FIG. 4A) of the outer housing 514, which may be a shell or other extrusion (including an aluminum extrusion), and may pass through the support housing (e.g., support fixture or skeleton) 512 within the outer housing 514 (which may provide structural support for the notched-tube heater 502 and oven chamber/heater housing 517) entering into a cavity 507 and creating a pressure drop which is detected by a pressure sensor 508. When this pressure drop is detected, the notched-tube heater 502 may be powered by passing an electric current through it via power leads 505, causing the notched or slotted region of the heater 502 to rapidly increase in temperature. The air being drawn into the cavity 507 may flow into the tube of the heater 502 and increase in temperature as it passes by the tube extensions and notched region 555. With the air passing through the notched region 555 of the heater 502, it begins to flow up past a thermocouple sensor 503 that is suspended close to a screen 515 at the bottom of the oven chamber 501. The screen 515 is perforated to allow the hot air to readily pass through the material in the oven chamber 501 before it exits the top of the oven and runs down side slots 509 formed by the housing 512 (e.g., support frame or skeleton) to the mouthpiece at the opposite end for inhalation by the user.

To minimize energy loss from the notched-tube heater 502, the heater 502 and the oven chamber 501 may be housed in a low thermally conductive material such as zirconia. The walls of the oven chamber/heater housing 517 may be relatively thin to reduce the amount of thermal mass associated with the material. As seen in FIG. 5A, there are small air gaps 504 between the oven chamber 501 and the housing 517 that may act as insulation (or could comprise an insulating material), aiding in the prevention of thermal sink (conduction) into the housing 517. This way, most of the energy, in the form of heat, will pass through the material to be vaporized as opposed to the body (e.g., the outer housing 514) of the device 500.

The heater 502 may be a resistive heating element that is heated by electric current passing between two terminals 505 to which the heater 502 is attached. The heater 502 may be an elongate tube (having any appropriate cross-sectional shape, including round, oval, rectangular, square, etc.) that is hollow; the tube may be straight, curved, bent (including doubling back on itself) and may include one or more cuts or openings in the lateral sides of the elongate tube through which air may be drawn. The tube of the heater 502 may be arranged generally transverse to the air path of the device so that drawing air from the mouthpiece pulls air through the cuts or openings, both heating the air and resulting in a turbulent airflow through the heater 502, which may mix the heated air to prevent local hotspots/cold spots.

The device 500 may also include a precision resistance measurement circuit to track resistance of the heater 502 when not heating and/or when heating to control the temperature of the heater 502 based on changes in the element's resistance from room temperature to vaporization temperatures. This measurement circuit may be a multi-terminal (e.g., four-terminal) sensing system that uses, e.g., two smaller leads 506 to sense the voltage drop across a region of the heater 502, e.g., across the notched region of the heating element, when a testing current (e.g., a small, but known, constant current) is applied through the testing leads 506. This applied testing current may be different than the heating current used to heat the heater 502 through power leads 505 to high temperatures and may be applied to the heater 502 when taking measurements between heating.

In the exemplary device 500, the measurement circuit may be configured to provide a four-point resistive measurement, and this circuit may in certain cases give a more accurate resistance measurement than a two-terminal resistive sensing circuit. A four-point measurement circuit may bypass the change in resistance the power leads experience from thermal conduction (as the power leads are welded to the heater tubes) and electrical heating from the high currents. In some configurations, a two-terminal resistance measurement circuit may not accurately compensate for the change in resistance of the power leads causing skewed results for the calculated temperature.

Figure 6:
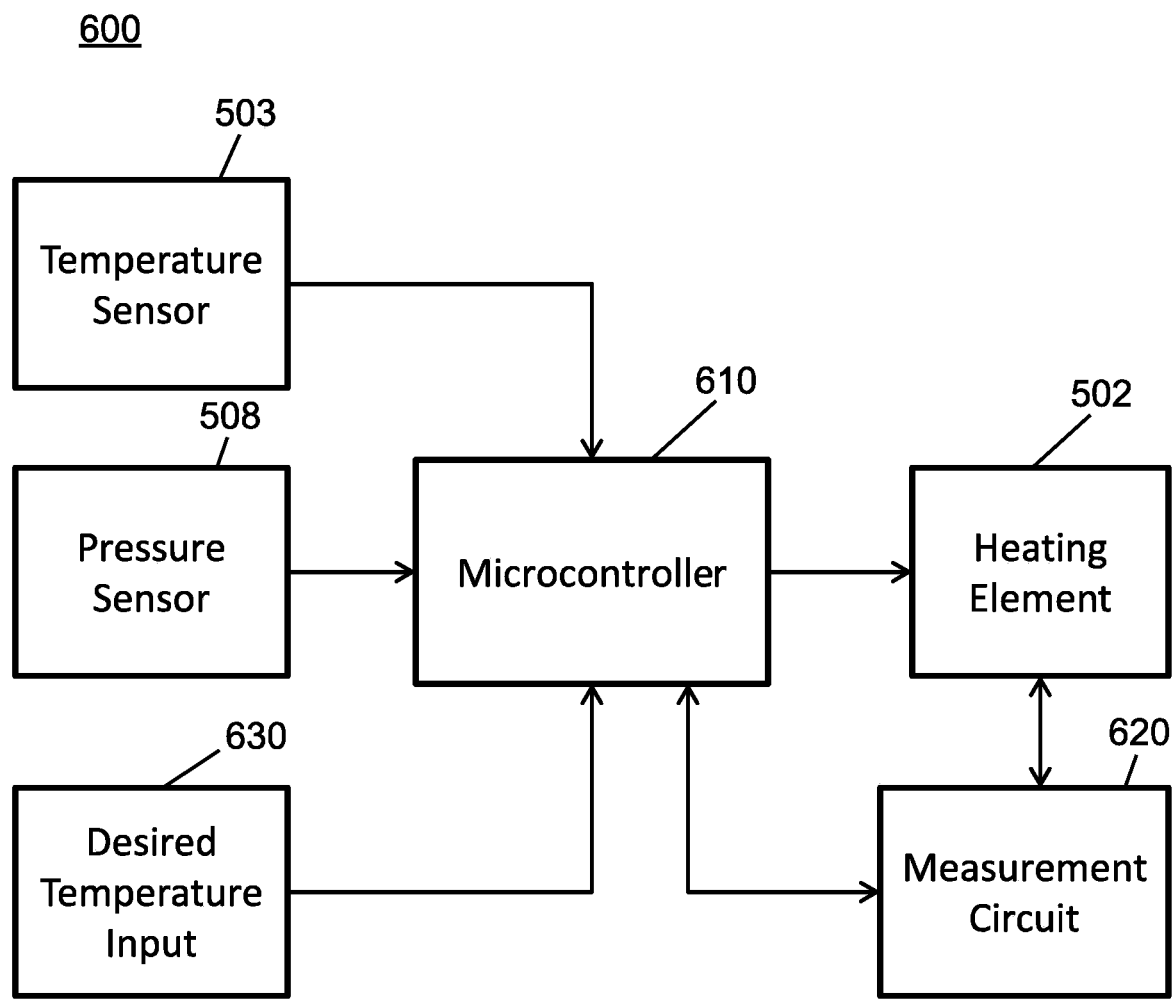
FIG. 6 illustrates features of a controller that may be adapted for regulating temperature in a vaporizer device consistent with implementations of the current subject matter.

FIG. 6 illustrates features of a controller that may be adapted for regulating temperature in a vaporizer device consistent with implementations of the current subject matter. Block diagram 600 includes a measurement circuit 620 that can measure the resistance of the resistive heater (e.g., heater 502) and provide an analog signal to a microcontroller 610. A device temperature, which can be inputted into the microcontroller 610 from temperature sensor 503 and an input from a sensor (e.g., pressure sensor 508, a button, or any other sensor) may be used by the microcontroller 610 to determine when the resistive heater 502 should be heated, e.g., when the user is drawing on the device or when the device is scheduled to be set at a warmer temperature (e.g., a standby temperature). In FIG. 6, a signal from the measurement circuit 620, an example of which is shown in FIG. 7, goes directly to the microcontroller 610.

The example of FIG. 6 consistent with implementations of the current subject matter provides for delivery of electrical energy from a power source, that may be part of the vaporizer 500, to the heater 502. Additionally, an additional input may be a desired temperature input 630, determined and inputted by a user and used as described below by the microcontroller 610. The desired temperature input, rather than inputted by a user, may be pre-established and inputted to the microcontroller 610.

Figure 7:
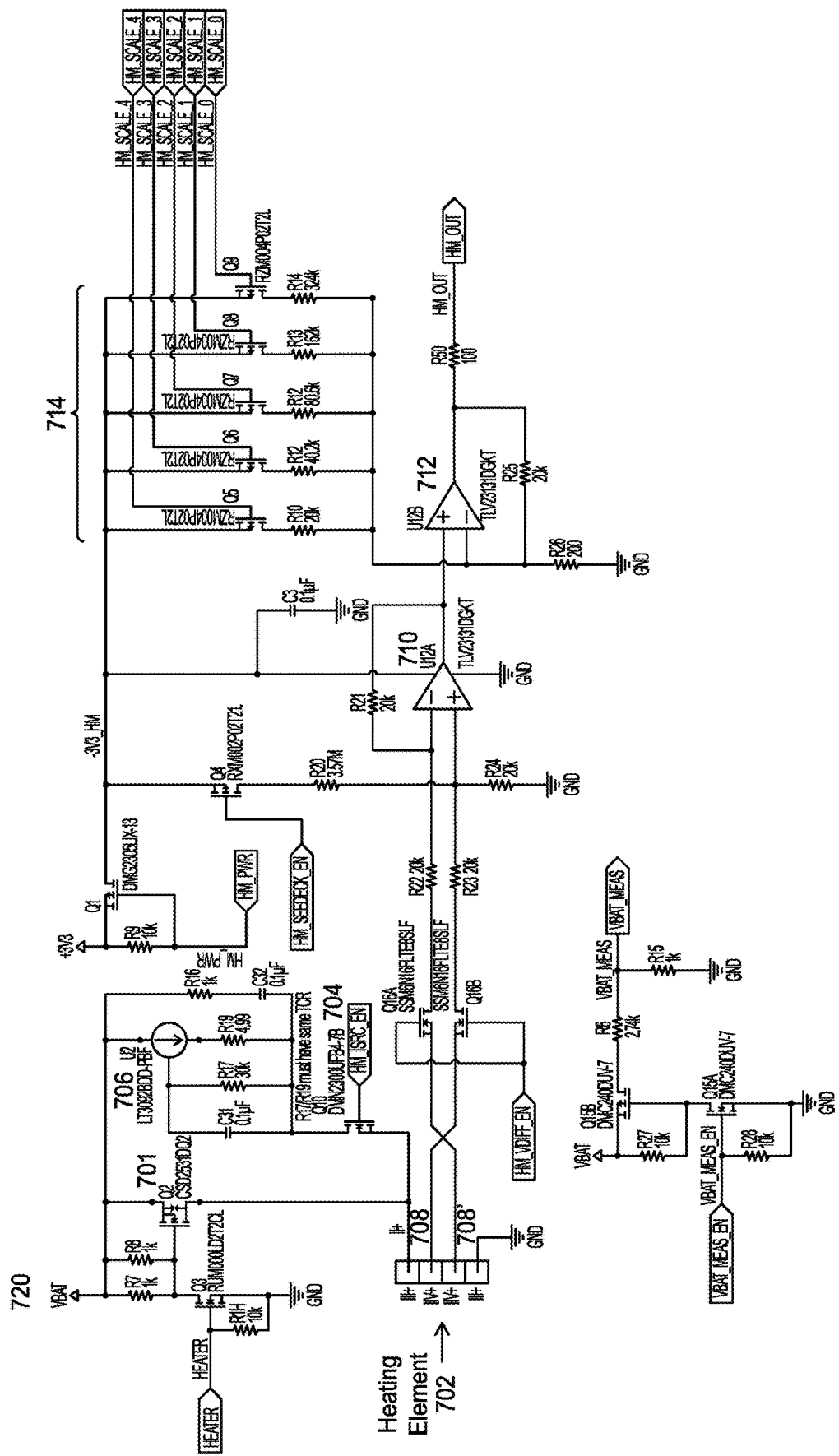
FIG. 7 illustrates features of a control circuit for regulating temperature in a vaporizer device consistent with implementations of the current subject matter.

FIG. 7 illustrates features of a control (e.g., measurement) circuit 620 for regulating temperature in a vaporizer device consistent with implementations of the current subject matter.

To accurately control the temperature of the resistive element during heating, it may be helpful for the resolution for the resistance measurements to be relatively precise. Based on the temperature coefficient of resistance (TCR) of the metal alloy used for the heating element, a change of only a few milliohms (mΩ) can represent a change of over 100° C. To achieve high resolution measurement of such temperature changes, a scalable resistance measurement circuit (e.g., a four-point resistance measurement circuit) may be used. FIG. 7 illustrates one example of a circuit schematic for a resistance measurement circuit configured as a four-point resistance measurement circuit. As shown in FIG. 7, power source 720 is provided. In operation, the circuit may enable MOSFET Q10 704, which allows a small current from current source U2 706 to pass through the heating element 702 (which is separately connected to the circuit by the terminals HI+ and HI− via power leads 505—FIG. 5A for providing the higher heating current), where a voltage drop across the heating element can be detected through the HV+ 708 and HV− 708' leads (via leads 506 shown in FIGS. 5A and 5B). This low voltage drop (in the low tens of millivolts) is sensed through the first stage of the amplifier circuit (U12A) 710, which can be configured as a differential amplifier with unity gain. Achieving the high resolution for resistance measurements comes from scaling the second stage of the amplifier circuit (U12B) 712. Selectable scaling factors 714 can selectably switch (under microprocessor 610 control) a specific combination of the MOSFETs Q5-Q9 to scale the input to the second stage amplifier, which can be set up as a non-inverting amplifier with a fixed gain, allowing for greater resolution of measurement of the heater's resistance. Scaling the second stage of the amplifier circuit as opposed to the first stage ensures that there will be little or no effect from the scaling resistors R10-R14 on the differential amplifier's closed-loop gain. This is desirable since the differential stage should preferably remain symmetric to accurately measure the differential voltage on the heating element. Also, this circuit has the capability to measure the thermoelectric, or Seebeck, effect that occurs when two dissimilar metals are at different temperatures. This may allow the vaporizer to compensate for the Seebeck effect. For example, using a microcontroller's analog-to-digital converter (ADC), the output voltage of the second stage amplifier may be sampled and converted to a binary representation, which may be used in a lookup table to convert these readings to a resistance. The lookup table may be determined theoretically (e.g., from an analysis of the circuit); and may be corrected with the measurements taken for the Seebeck effect along with some fixed offset that arises from component tolerances.

The vaporizers consistent with some implementations of the current subject matter may regulate and adjust the air temperature applied to the vaporizable material. In any of the variations described herein, the vaporizer devices may be configured to allow the user to choose (Desired Temperature Input 630) different air temperatures for vaporizing the material of interest (e.g., by a button or other control input on the device, or wirelessly, e.g., through a user interface on a remote device such as a smartphone that is in communication with the vaporizer). The vaporizer control circuitry (e.g., the block diagram 600 of FIG. 6) may include one or more controllers to regulate overall temperature selection.

In particular, the device controller 610 can regulate the temperature of the heating element 502 (resistive heater) using a first controller circuit (control law) to control and rapidly heat the resistive heater and estimate its temperature based on the TCR of the resistive heater; and a second controller circuit (control law) may further regulate the resistive heater based on the user-selected or predetermined vaporization temperature (e.g., between 200° C. and 500° C.), which may be sensed by one or more thermocouples 503 in the airflow path (e.g., downstream from the resistive heater and/or between the resistive heater and the oven chamber). These two controller circuits may cooperate together to adjust the heating temperature or rate of increase of heating by modulating the duty cycle of the energy applied to the heater.

For example, a proportional-integral-derivative controller (PID controller) may be implemented on the microcontroller 610 that monitors the thermocouple sensor 503 above the heating element 502 and uses this as the feedback mechanism for the air temperature controller. Separately, another second PID controller may be used to regulate the temperature of the heating element 502 using the TCR of the metal alloy (of the resistive heater) to determine the target resistance set point of the heater so that it does not exceed a safe operating point. These two PID controllers may be run simultaneously, e.g., at 128 Hz, and control logic may be used to determine which PID controller (air temperature or heater temperature) output to use at any given point. The output for both of the PID controllers may be alternated in a duty cycle of the PWM signal input to the power MOSFET 701 (e.g., Q2 in the schematic of FIG. 7), with only one output at a time used to control the transistor. When the device detects that the user has started a puff, which may be determined from a sensor such as a pressure sensor (see, e.g., FIG. 5A, 508) (or from a button pressed by the user), the TCR-sensed heater temperature PID controller may be initiated first. This may ensure that the temperature of the heating element rapidly increases to its maximum operating temperature to heat the incoming air as quickly as possible. As mentioned, the temperature of the thermocouple 503 is monitored and when this crosses a predetermined threshold, the output of the air temperature PID controller is then applied. For example, if the user sets the vaporization temperature to 350° C. and proceeds to draw on the device (tripping the pressure sensor's threshold for the start of a puff), this causes the microcontroller to begin to pulse the power MOSFET using the duty cycle from the heater temperature PID controller to regulate the heating element's temperature to the maximum value allowed of 700° C. As the incoming air is heated, the air temperature PID controller then controls applied heater current once the air temperature detected crosses a set threshold value (e.g., corresponding to a temperature of, for example, 300° C.). The heating element is then controlled via the air temperature PID controller to regulate the air temperature to 350° C., but the heater temperature PID controller will not allow the temperature of the heating element to exceed the 700° C. cutoff. The system can alternate the two PID controllers if the airflow is low enough to allow the heating element to reach the maximum allowed safe operating temperature. That is, if the airflow is too high, the heater may not be able to reach its maximum temperature.

Figure 8:
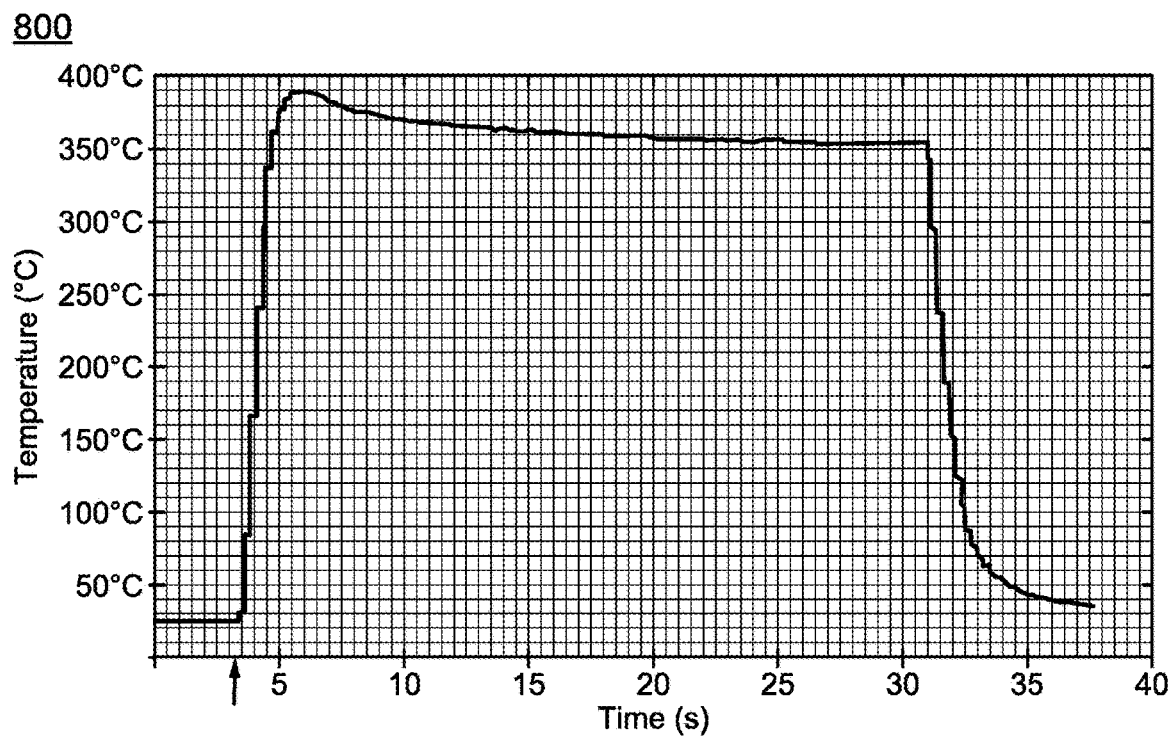
FIG. 8 shows a graph illustrating a temperature profile of air in a vaporizer device consistent with implementations of the current subject matter.
Figure 9:
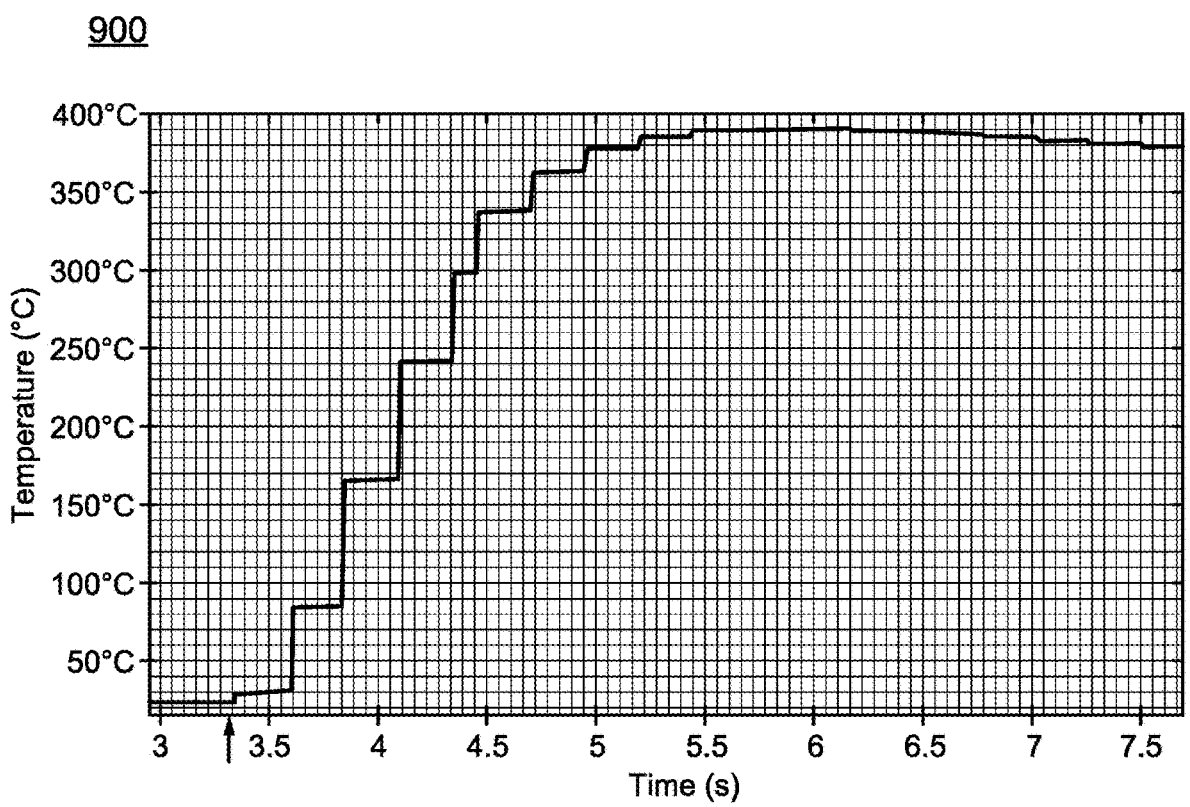
FIG. 9 shows a more detailed view of a portion of the graph of FIG. 8.

Embodiments described above were tested, using an airflow of 4 L/min passing through the heating element and oven, while data from the thermocouple was recorded during the session. As seen in the graphs 800 and 900 of FIGS. 8 and 9, respectively, the thermocouple reaches vaporization temperatures in approximately one second (FIG. 9 shows a more detailed plot of between three and seven seconds from FIG. 8, showing the heat up time). The control law running on this device uses the resistance measurements of the heating element to ensure that the element never exceeds a safe operating temperature (e.g., 700° C.). The device continuously monitors the thermocouple and regulates the air temperature to a set value (350° C. in this example). There is an overshoot on the heat up, but this can be intentional, to get the vaporizable material up to vaporization temperatures as quickly as possible. The coarse resolution on the data below is due to the minimum sample time of the thermocouple monitor used in the device. However, it is enough to control the air temperature to within at least ±5° C. Finer grained control systems are also within the scope of the present subject matter.

In some variations of the on-demand convection-based vaporizers described herein, the resistive heater (resistive heating element) may be formed of one or more different types of metal alloys, such as stainless steel 316, stainless steel 309, Nichrome, or any other resistive metal alloy. Alternatively or in addition, the housing for the resistive heating element and oven may be made from a metal or alloy, such as a thin piece of aluminum or stainless steel. The heating element may be insulated from the housing by a sleeve or bushing made from Teflon or similar material.

In any of the variations described herein, the vaporizer may include a heat exchanger in thermal communication with the heater, which may achieve better efficiency. This may involve a circular type of metal baffling or disc that may be inserted into each side of the heating element's tube and mounted close to the notched region, such as the notched region 555. Some of the heat that is being conducted down the tube away from the notched region may also be conducted into these heat exchangers. As the air is drawn in through the ends of the tube, these alternate proposed heat exchangers may utilize some of the lost heat being conducted down the ends of the tube and put this otherwise "lost" energy back into the drawn air. Another method similar to such discs or baffling would include raised portions of the heater tube, or fins, that protrude in towards the center of the tube. These fins can provide another style of heat exchanger to help add heat back into the air path.

Consistent with some implementations of the current subject matter, a thermocouple may be built into the vaporizer rather than incorporating a thermocouple sensor 503 in the vaporizer 500. In one example, as a surrogate for taking the air temperature measurement with a thermocouple, a temperature of the screen 515 can be measured. For example, if the screen 515 is electrically isolated from the oven chamber 501, it can be used as a thermistor. By inclusion of a lead coming off of either end along the long axis via which the resistance can be measured. This approach allows the microcontroller 610 to calculate the average temperature of the screen 515, which may be used as an alternative to an air temperature measurement as they should be highly correlated. As another example, if the screen 515 stays electrically connected to the oven chamber 501, a single lead of a dissimilar material can be pulled off of the screen 515, creating an ad hoc thermocouple. By measuring the voltage across the oven chamber/screen construction and the lead of dissimilar material, the temperature at the junction between the two materials can be calculated by the microcontroller 610. Or, an infrared sensor within or near the oven chamber can similarly measure the temperature of the air vaporizing the material. Alternatively, the downstream air temperature sensor can be removed outright and an algorithm could be used to predict the downstream air temperature as a function of the heater temperature, flow rate, and/or time.

Consistent with some implementations of the current subject matter, the oven chamber and the mouthpiece of a vaporizer are not required to be on opposing ends of the vaporizer. For example, the mouthpiece may be adjacent or near adjacent the oven chamber. In such a configuration, the one or more air paths from the oven chamber connected to the mouthpiece, through which the vapor travels, can be configured to allow for the vapor to sufficiently cool before being provided to a user via the mouthpiece. For example, a turbulent path for the air flow after the oven chamber may be provided to allow for sufficient cooling. Such a turbulent path may include a zig-zag path, a path with various bumps and/or projections, or other configurations or methods, to allow for the relatively quick exchange of heat away from the heated vapor.

Figure 10:
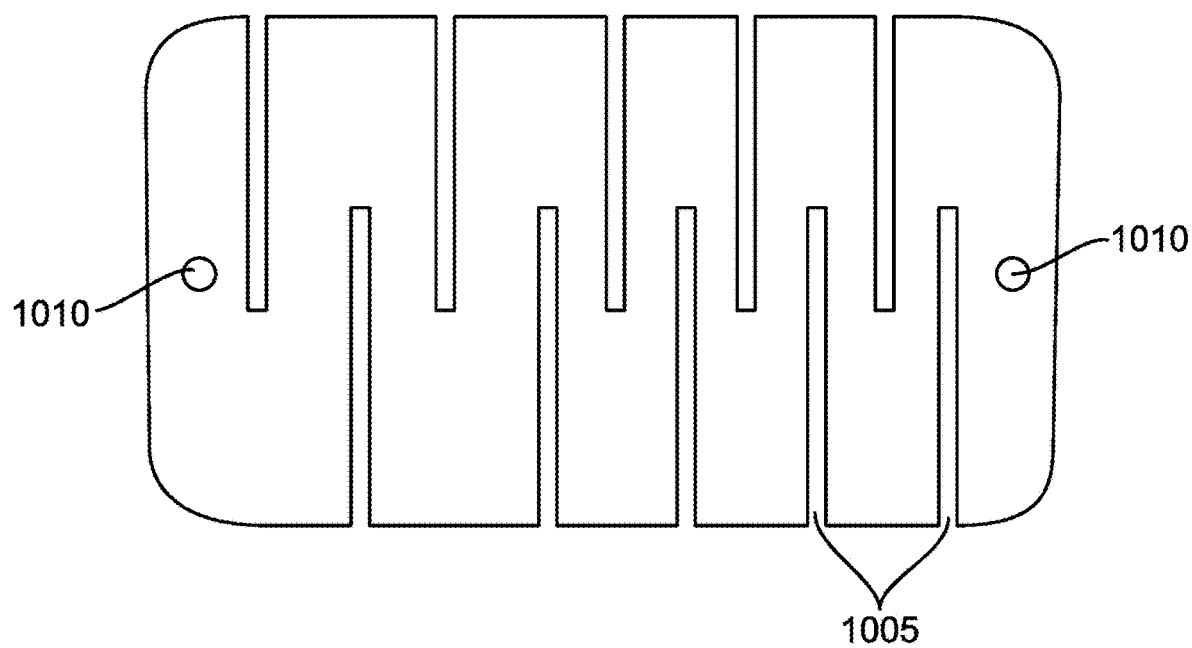
FIG. 10 illustrates features of an exemplary heater for use with a vaporizer device consistent with implementations of the current subject matter.

FIG. 10 shows another variation of a heater element 1000, in which the heater is a flat-plate heater that has a thin serpentine design made from a resistive metal alloy, for example. This design may replace the heater 302 shown in FIGS. 3-4E. In this design, the flat heating element may be placed directly in the air path below the oven chamber. Instead of the air path passing through a tube and then changing direction to exit the tube from a notched region, as described above in reference to FIGS. 5A and 5B, in FIG. 10 the air path may be much more direct. The air may enter the device from below the heater serpentine element 1000 and pass through slots 1005 in the heater 1000 before entering the oven chamber. A thermocouple may be mounted between the heater and the oven chamber, as in FIG. 5A, to measure and control the air temperature before contacting or otherwise heating the vaporizable material. In some variations, the heater (resistive heating element) may be a thin-film resistive heating element that is coiled, bent, or otherwise arranged in a 3D structure having an appropriate number (e.g., 1, 2, 3, 5, etc.) of channels, slits, slots, etc. therethrough to allow air to flow over and through the resistive heater for rapid heating. In any of these variations, the resistive heater 1000 may be held in the air path, and coupled to the inner chamber of the device by a small number of contact points 1010 to minimize thermal transfer; alternatively the heater 1000 may be connected by thermally and/or electrically insulating couplings. In any of these variations, the channels, slits, etc. or surface area of the heater can have fractal, jagged, finned or other features to further increase heat transfer to the air.

Figure 11:
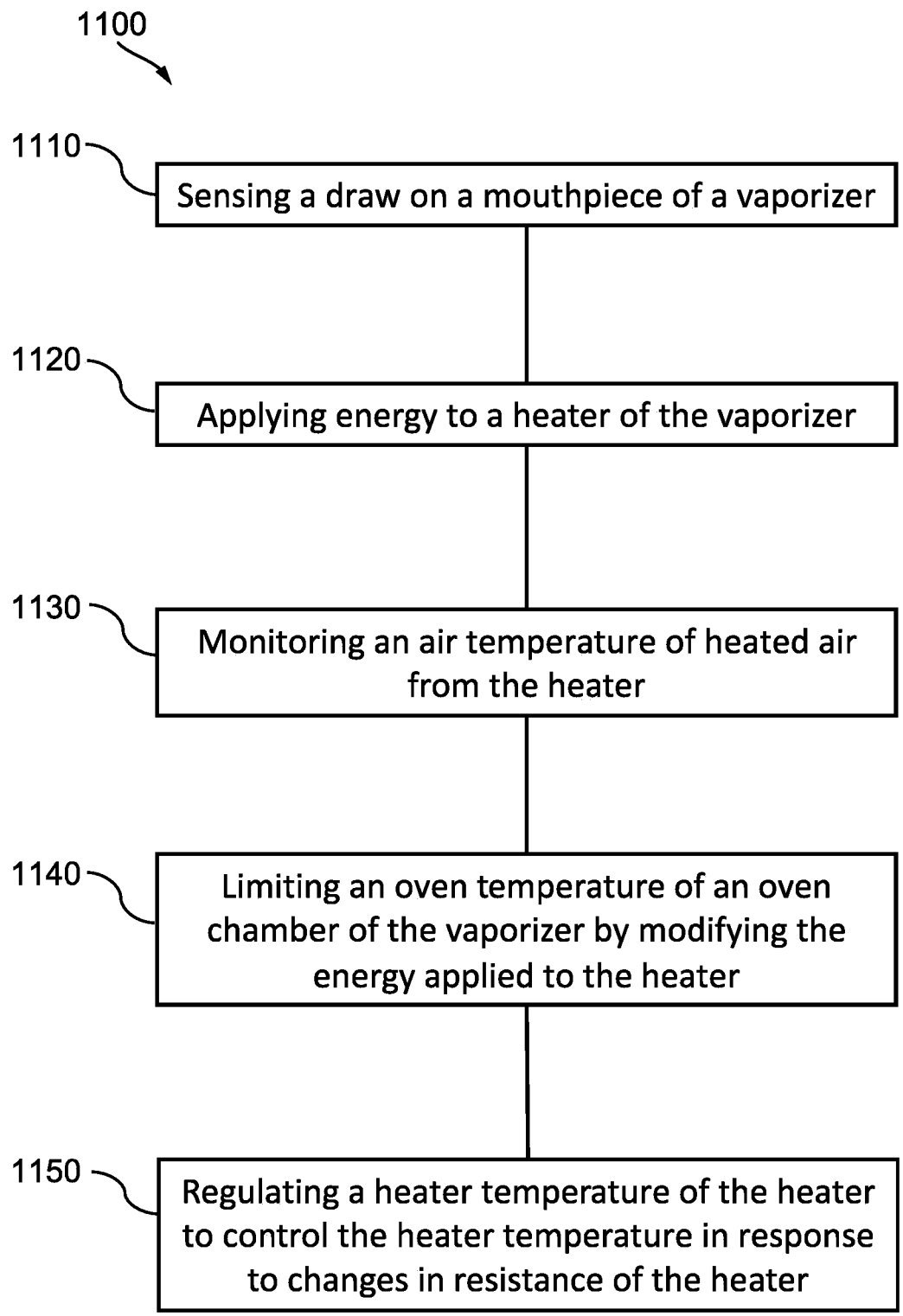
FIG. 11 shows a process flow chart illustrating features of a method of regulating and adjusting air temperature applied to vaporizable material in a vaporizer device consistent with implementations of the current subject matter.

With reference to FIG. 11, a process flow chart 1100 illustrates features of a method, which may optionally include some or all of the following. At 1110, a draw on a mouthpiece by a user of a vaporizer is detected (or, alternatively, a button or other start indicator device can be selected by the user). This detection may be via a pressure sensor in an airflow path of ambient air entering a cavity of the vaporizer. At 1120, energy is applied to a heater of the vaporizer, which begins the process of rapidly increasing the heater to a high or maximum operating temperature to quickly heat incoming ambient air. At 1130, an air temperature of heated air from the heater is monitored. This monitoring may be through one or more thermocouple sensors between the heater and an over chamber of the vaporizer, to determine the temperature of air leaving the heater. At 1140, an oven temperature of the oven chamber of the vaporizer is limited by modifying the energy applied to the heater. This may ensure that the heater does not exceed a predetermined threshold. At 1150, a heater temperature of the heater is regulated to control the heater temperature in response to changes in resistance of the heater.

As discussed above, implementations of the current subject matter include methods and apparatuses for vaporizing materials so that they may be inhaled by a user. The apparatuses described herein include vaporizer devices and systems including vaporizer devices. In particular, described herein are on-demand convection vaporizer apparatuses (devices and systems) that may be configured for user control and operation. The following descriptions of example implementations are provided for illustration of various features that may be part of the current subject matter. They are not intended to be limiting.

For example, on-demand, hand-held convection vaporizer devices may include: an elongate body having a shell; a mouthpiece on the elongate body; a sensor to detect draw through the mouthpiece; an oven chamber within the elongate body, wherein the oven chamber's lateral walls are surrounded by an air gap; a convection heater within the elongate body, the convection heater having a plurality of slots and/or openings configured to pass air over the convection heater and generate a mixing turbulence as air is passed over and/or through the convection heater; a heater control circuit, the heater control circuit configured to heat the convection heater to a temperature of greater than 500° C. upon detection of draw through the mouthpiece; further wherein the heater control circuit limits the heater to maximum temperature; further wherein air flowing into the oven chamber from the heater is heated to a target vaporization temperature.

An on-demand, hand-held convection vaporizer device may include: an elongate body having a shell; a mouthpiece at a proximal end of the elongate body; a sensor to detect draw through the mouthpiece; an oven chamber at a distal end of the elongate body, wherein greater than 80% of the oven chamber's lateral walls are surrounded by an air gap; a convection heater within the elongate body, the convection heater having a plurality of slots and/or openings configured to pass air over the convection heater and generate mixing turbulence as air is passed over and/or through the convection heater; a heater control circuit, the heater control circuit configured to heat the convection heater to a temperature of greater than 500° C. upon detection of draw through the mouthpiece; further wherein the heater control circuitry limits the heater to maximum temperature; wherein air flowing into the oven chamber from the heater is heated to a target vaporization temperature of greater than 200° C. within 4 seconds of detection of draw through the mouthpiece.

Any of these vaporizers may use a tubular convection heater such as an elongate tube extending in a long axis, the tube having a plurality of cut-out regions along its length therethrough to generate turbulence in air passing therethrough. For example, described herein are on-demand, hand-held convection vaporizer devices that may include: an elongate body having a shell; a mouthpiece at a proximal end of the elongate body; a sensor to detect draw through the mouthpiece; an oven chamber at a distal end of the elongate body, wherein greater than 80% of the oven chamber's lateral walls are surrounded by an air gap; a convection heater including an elongate tube extending in a long axis, the tube having a plurality of cut-out regions along its length therethrough to generate turbulence in air passing therethrough; a heater control circuit, the heater control circuit configured to heat the convection heater to a temperature of greater than 500° C. upon detection of draw through the mouthpiece; further wherein the heater control circuitry limits the heater to maximum temperature; wherein air flowing into the oven chamber from the heater is heated to a target vaporization temperature of greater than 200°.

Any of the vaporizers and/or methods according to implementations of the current subject matter may also include or make use of a heater control circuit including a four-point measurement circuit. For example, an on-demand, hand-held convection vaporizer device may include: an elongate body having a shell; a mouthpiece at a proximal end of the elongate body; a sensor to detect draw through the mouthpiece; an oven chamber at a distal end of the elongate body, wherein the oven chamber's lateral walls are surrounded by an air gap; a convection heater having a plurality of slots and/or openings along its length therethrough to generate turbulence in air passing therethrough; a heater control circuit, the heater control circuit including a four-point measurement circuit having four leads coupled to the convection heater, wherein two of the leads are configured to sense the voltage drop across a region of the heating element, further wherein the heater control circuit is configured to heat the convection heater to a temperature of greater than 500° C. upon detection of draw through the mouthpiece and to limit the heater to maximum temperature; wherein air flowing into the oven chamber from the convection heater is heated to a target vaporization temperature.

Thus in general, when the device includes a four-point measurement circuit having four leads coupled to the convection heater, two of the leads may be configured to sense the voltage drop across a region of the heating element; these leads may be between two outer leads. The two outer leads may apply power to the convection heater. For example, a first lead and second lead of the four leads of the heater control circuitry may be configured to apply power to heat the convection heater. The two leads configured to sense the voltage drop may be spaced apart from the power-applying leads so that the temperature increase due to the high levels of power applied will not impact the resistance/conductivity of the voltage-sensing leads.

Any of the vaporizers according to implementations of the current subject matter may include a temperature sensor between the convection heater and an inside of the oven chamber, wherein the temperature sensor provides air temperature input to the heater control circuitry.

In general, the heater control circuitry may be configured to control the energy applied to the convection heater based on a temperature of the convection heater and based on a temperature of the air between the convection heater and the oven chamber.

In any of these devices, the mouthpiece may be at a proximal end of the elongate body and the oven chamber may be within the distal end of the elongate body.

The devices according to implementations of the current subject matter may be configured to immediately or near-instantaneously heat air to vaporize a material in the oven chamber. For example, air flowing into the oven chamber from the heater may be heated to a target vaporization temperature of greater than 200° C. within 4 seconds (e.g., within 3 second, within 2 seconds, within 1 second, etc.) of detection of draw through the mouthpiece.

A chamber's lateral walls may be surrounded by an air gap such that the chamber's lateral (e.g., side walls, perpendicular to the bottom of the oven chamber) are at least 50% surrounded by the air gap (e.g., at least 60%, at least 65%, at least 70%, at least 75%, at least 80%, at least 85%, at least 95% surrounded, etc.).

Methods of operating any of the apparatuses described herein may include methods of vaporizing materials. For example, methods of operating an on-demand, hand-held convection vaporizer may include features such as: sensing a draw on a mouthpiece of the vaporizer; applying energy to a conductive heater of the vaporizer; adjusting the energy applied to the conductive heater based on a four-point measurement including a first pair of inputs corresponding to a first pair of leads connected to the conductive heater and a second pair of inputs corresponding to a second pair of leads connected to the conductive heater wherein the second pair of leads are offset from the first pair of leads; and vaporizing a vaporizable material within the oven chamber of the vaporizer.

Applying energy to the conductive heater of the vaporizer may include increasing the temperature by more than 200 degrees within about one second, and/or applying energy from the first pair of leads. The second pair of leads may be positioned between the first pair of leads.

Any of these methods may also include determining a temperature of the conductive heater from the four-point measurement.

Adjusting the energy applied to the conductive heater based on the four-point measurement may include adjusting the frequency and/or duty cycle of the energy applied to the conductive heater.

Any of these methods may also include adjusting the energy applied to the conductive heater based on a temperature of the air between the convection heater and an oven chamber of the vaporizer, and/or sensing the temperature of the air between the convection heater and the oven chamber of the vaporizer.

Any of these methods may also include limiting the energy applied to the conductive heater so that the temperature of the conductive heater does not exceed a maximum threshold (e.g., 500° C., 550° C., 600° C., 650° C., 700° C., 750° C., etc.).

For example, a method of operating an on-demand, hand-held convection vaporizer may include: sensing a draw on a mouthpiece of the vaporizer; applying energy to a conductive heater of the vaporizer from a first pair of leads to increase the temperature by more than 200 degrees within about one second; adjusting the energy applied to the conductive heater based on a four-point measurement including a first pair of inputs that corresponds to the first pair of leads and a second pair of inputs corresponding to a second pair of leads connected to the conductive heater wherein the second pair of leads that are positioned between the first pair of leads; adjusting the energy applied to the conductive heater based on a temperature of the air between the convection heater and an oven chamber of the vaporizer; and vaporizing a vaporizable material within the oven chamber of the vaporizer.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaporizer, comprising:
   an outer housing;
   a structural housing configured to fit within the outer housing, the structural housing comprising:
     a heater configured to heat air passing the heater, wherein the air is configured to enter the outer housing and the structural housing via an inlet air opening formed at least in part by the outer housing; and
     an oven chamber configured to hold a vaporizable material to be heated by the heated air, causing the vaporizable material to at least partially vaporize into the heated air;
   a mouthpiece coupled to the outer housing; and
   a cooling pathway formed between the outer housing and the structural housing, the cooling pathway configured to cool and deliver the heated air and vaporized vaporizable material to the mouthpiece.

2. The vaporizer of claim 1, wherein the cooling pathway defines a turbulent air path configured to cool the heated air and vaporized vaporizable material.

3. The vaporizer of claim 1, wherein the heater comprises a convection heater configured to heat the air to a vaporization temperature to at least partially vaporize the vaporizable material; and wherein the convection heater is configured to heat the air to the temperature within three seconds.

4. The vaporizer of claim 1, further comprising the inlet air opening, wherein the inlet air opening is formed through a portion of the outer housing through which the air passes to the heater.

5. The vaporizer of claim 1, wherein the heater comprises an elongate tube comprising a notched region along at least a portion of a length of the elongate tube.

6. The vaporizer of claim 1, wherein an air gap is formed around walls of the oven chamber.

7. The vaporizer of claim 1, wherein the oven chamber comprises side walls; and wherein a portion of an outer surface of the side walls is surrounded by one or more of an air gap and an insulating material.

8. The vaporizer of claim 1, further comprising a screen positioned within the oven chamber at a bottom portion of the oven chamber; wherein the screen comprises a plurality of perforations to allow the heated air to pass to the oven chamber.

9. A vaporizer comprising:
   an outer housing;
   a heater positioned within at least a portion of the outer housing and configured to heat air passing the heater, wherein the air is configured to enter the outer housing via an inlet air opening formed at least in part by the outer housing;
   an oven chamber positioned within at least a portion of the outer housing and configured to hold a vaporizable material to be heated by the heated air, causing the vaporizable material to at least partially vaporize into the heated air to form a heated vapor;
   a mouthpiece coupled to the outer housing; and
   a turbulent air path positioned within at least a portion of the outer housing and configured to deliver the heated vapor to the mouthpiece, the turbulent air path further configured to increase the exchange of heat away from the heated vapor, improving the cooling of the heated vapor delivered to the mouthpiece.

10. The vaporizer of claim 9, wherein the heater comprises a convection heater configured to heat the air to a vaporization temperature to at least partially vaporize the vaporizable material; and wherein the convection heater is configured to heat the air to the temperature within three seconds.

11. The vaporizer of claim 9, further comprising: the inlet air opening, wherein the inlet air opening is formed through a portion of the outer housing through which the air passes to the heater.

12. The vaporizer of claim 9, wherein the heater comprises an elongate tube comprising a notched region along at least a portion of a length of the elongate tube.

13. The vaporizer of claim 9, wherein an air gap is formed around walls of the oven chamber.

14. The vaporizer of claim 9, wherein the oven chamber comprises side walls; and wherein a portion of an outer surface of the side walls is surrounded by one or more of an air gap and an insulating material.

15. The vaporizer of claim 9, further comprising a screen positioned within the oven chamber at a bottom portion of the oven chamber; wherein the screen comprises a plurality of perforations to allow the heated air to pass to the oven chamber.

16. The vaporizer of claim 9, wherein the heater comprises a glass material.

\* \* \* \* \*